(12) United States Patent
Kataoka et al.

(10) Patent No.: US 9,320,433 B2
(45) Date of Patent: Apr. 26, 2016

(54) LIVING BODY DETECTION SENSOR, COMMUNICATION APPARATUS HAVING LIVING BODY DETECTION SENSOR, METAL DETECTION SENSOR

(71) Applicant: Kabushiki Kaisha Toshiba, Minato-ku, Tokyo (JP)

(72) Inventors: Kazuki Kataoka, Kanagawa-ken (JP); Takafumi Ohishi, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 30 days.

(21) Appl. No.: 14/163,754

(22) Filed: Jan. 24, 2014

(65) Prior Publication Data

US 2015/0038864 A1     Feb. 5, 2015

(30) Foreign Application Priority Data

Aug. 1, 2013   (JP) .................................. 2013-160021

(51) Int. Cl.
*A61B 5/00* (2006.01)
*A61B 5/0402* (2006.01)

(52) U.S. Cl.
CPC .............. *A61B 5/0006* (2013.01); *A61B 5/0402* (2013.01); *A61B 5/725* (2013.01)

(58) Field of Classification Search
CPC .......... A61B 5/00; A61B 5/0006; A61B 5/04; A61B 5/0402
USPC .......................................................... 600/509
See application file for complete search history.

(56) References Cited

U.S. PATENT DOCUMENTS

| 6,223,018 | B1 | 4/2001 | Fukumoto et al. |
| 9,026,059 | B2* | 5/2015 | Shi ........................ H04B 1/3838 455/550.1 |
| 2003/0172136 | A1* | 9/2003 | Katagawa et al. ............. 709/220 |
| 2005/0143669 | A1* | 6/2005 | Matsumura et al. ........... 600/509 |
| 2005/0192727 | A1* | 9/2005 | Shostak et al. ................... 701/37 |
| 2007/0040545 | A1* | 2/2007 | Takiguchi ............... G01S 11/06 324/76.11 |
| 2007/0043304 | A1* | 2/2007 | Katayama ..................... 600/549 |
| 2007/0184788 | A1* | 8/2007 | Minotani et al. .............. 455/117 |
| 2008/0123599 | A1 | 5/2008 | Ishibashi et al. |
| 2009/0240520 | A1* | 9/2009 | Takano et al. ...................... 705/2 |
| 2010/0062709 | A1* | 3/2010 | Kato ............................ 455/41.1 |

(Continued)

FOREIGN PATENT DOCUMENTS

| JP | 10-229357 A | 8/1998 |
| JP | 2001007735 A | 1/2001 |

(Continued)

*Primary Examiner* — Christopher A Flory
(74) *Attorney, Agent, or Firm* — White & Case LLP

(57) ABSTRACT

According to one embodiment, a living body detection sensor includes a substrate, a signal generation unit, a first conductor, a second conductor, and a detection unit. The substrate includes a reference potential electrode and a dielectric material. The signal generation unit generates a first signal, the signal generation unit is provided on the substrate. The first conductor receives the first signal, the first conductor is separated from the substrate. The second conductor t receive the first signal sent from the first conductor, the second conductor is separated from the substrate. The detection unit receives the first signal outputted from the second conductor and detects an electric field produced between the first conductor and the second conductor, the detection unit is provided on the substrate. The living body detection sensor detects whether a living body is close to the living body detection sensor.

15 Claims, 22 Drawing Sheets

(56) References Cited

U.S. PATENT DOCUMENTS

| | | | |
|---|---|---|---|
| 2010/0292568 A1* | 11/2010 | Droitcour | A61B 5/05 600/425 |
| 2011/0227856 A1* | 9/2011 | Corroy | H04B 13/005 345/173 |
| 2012/0029369 A1* | 2/2012 | Icove et al. | 600/504 |
| 2013/0013026 A1* | 1/2013 | Hoyer et al. | 607/49 |
| 2014/0070957 A1* | 3/2014 | Longinotti-Buitoni et al. | 340/870.01 |
| 2014/0074186 A1* | 3/2014 | Faltys | A61N 1/36053 607/61 |
| 2015/0057722 A1* | 2/2015 | Faltys | A61N 1/36053 607/61 |
| 2015/0126825 A1* | 5/2015 | LeBoeuf et al. | 600/301 |

FOREIGN PATENT DOCUMENTS

| | | |
|---|---|---|
| JP | 2001077735 A | 3/2001 |
| JP | 2003037566 A | 2/2003 |
| JP | 2005079900 A | 3/2005 |

\* cited by examiner

12 # LIVING BODY DETECTION SENSOR, COMMUNICATION APPARATUS HAVING LIVING BODY DETECTION SENSOR, METAL DETECTION SENSOR

CROSS REFERENCE TO RELATED APPLICATION

This application is based upon and claims the benefit of priority from the prior Japanese Patent Application No. 2013-160021, filed on Aug. 1, 2013, the entire contents of which are incorporated herein by reference.

FIELD

Embodiments described herein relate to a living body detection sensor, a communication apparatus having the living body detection sensor, and a metal detection sensor.

BACKGROUND

Living body communication in which communication data are transmitted and received through living bodies such as human bodies has been drawing attention. The living body communication is expected to be applied to medical and health care services, short-range wireless communication practices, in-vehicle wireless communication operations, amusement activities, and the like. The living body communication can significantly reduce power consumption as compared to some conventional communication techniques.

In the living body communication, each communication apparatus configured to use a living body as part of a transmission path is provided with two electrodes. One is a signal electrode connected to a signal line, and the other is a reference potential electrode connected to ground potential of the communication apparatus having reference potential. The signal electrodes of the respective communication apparatuses are electrically connected together mainly through the living body, while the reference potential electrodes of the respective communication apparatuses are electrically connected together mainly through the space or the earth. Thereby, each communication apparatus transmits the potential difference between the signal electrode and the reference potential electrode to the counterpart communication apparatus.

Each communication apparatus to perform the living body communication uses the electrostatic coupling between the electrodes and the surface of the living body. Accordingly, the capacitance value of the electrodes decreases as the distance of the communication apparatus from the surface of the living body becomes larger. A potential effective solution to the decrease in the capacitance value of the electrode is the enlargement of the area of each electrode, or adoption of a variable capacitance element. However, a problem with the enlargement of the electrode area is that the size of the electrode area is restricted by an apparatus that embeds the electrodes. Meanwhile, the adoption of the variable capacitance element poses a problem that the communication is likely to take place even if there is no living body around the apparatus unless a distance between the apparatus and such a living body is recognizable.

For this reason, a living body detection sensor capable of recognizing the distance between an apparatus and a living body is essential for the apparatus to perform the living body communication. Furthermore, the living body detection sensor is applicable as a metal detection sensor to detect the location and shape of a piece of metal which is implanted in an object.

DETAILED DESCRIPTION

Figure 1:
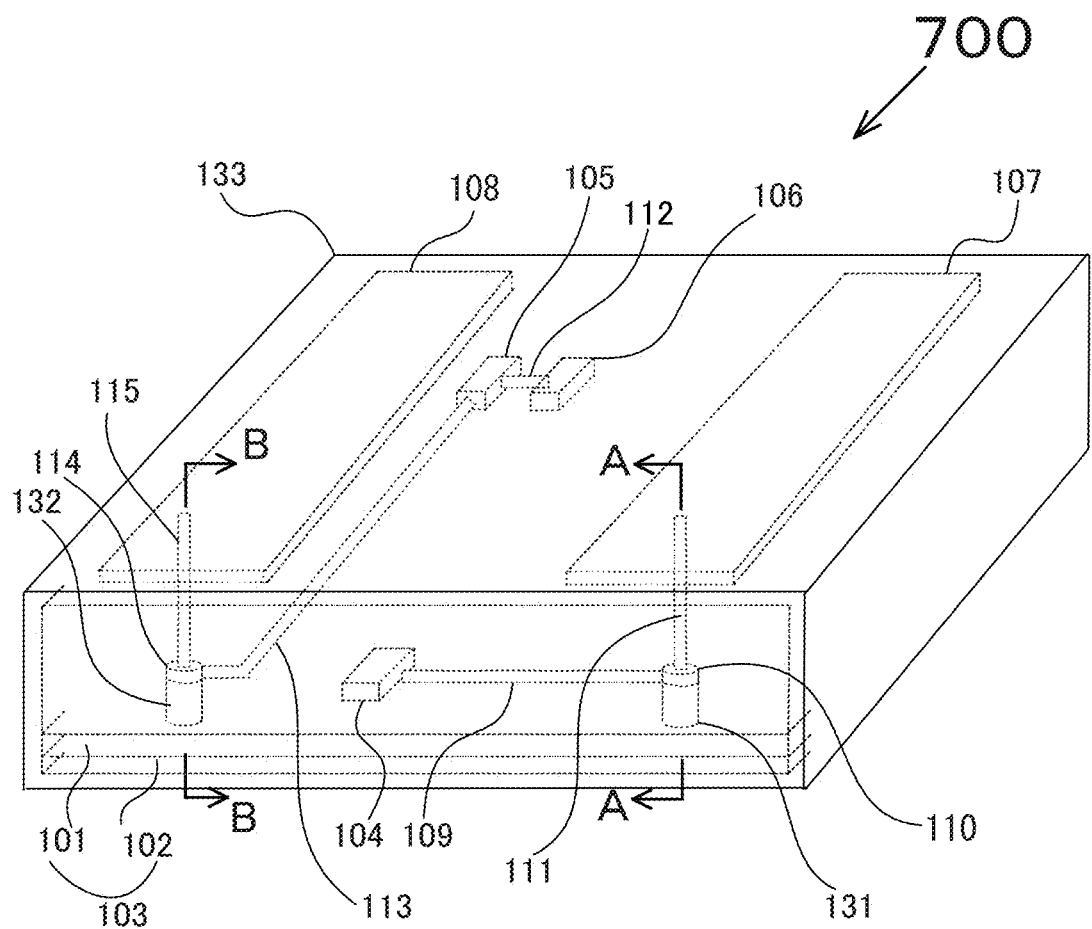
FIG. 1 is a diagram showing a configuration of a living body detection sensor according to a first embodiment.

According to one embodiment, a living body detection sensor includes a substrate, a signal generation unit, a first conductor, a second conductor, and a detection unit. The substrate includes a reference potential electrode and a dielectric material. The signal generation unit generates a first signal, the signal generation unit is provided on the substrate. The first conductor receives the first signal, the first conductor is separated from the substrate. The second conductor t receive the first signal sent from the first conductor, the second conductor is separated from the substrate. The detection unit receives the first signal outputted from the second conductor and detects an electric field produced between the first conductor and the second conductor, the detection unit is provided on the substrate. The living body detection sensor detects whether a living body is close to the living body detection sensor.

According to another embodiment, a communication apparatus includes a substrate, a communication unit, a first conductor, a second conductor, a detection unit, a variable capacitance element, a control unit, and a magnetic field transmitting and receiving unit. The substrate includes a reference potential electrode and a dielectric material. The communication unit transmits and receives a signal, the communication unit is provided on the substrate. The first conductor is separated from the substrate and connected to the communication unit. The second conductor receives a first signal sent from the first conductor, the second conductor is separated from the substrate. The detection unit receives the first signal outputted from the second conductor and detects an electric field produced between the first conductor and the second conductor, the detection unit is provided on the substrate. The variable capacitance element is provided on the substrate, one end of the variable capacitance element is connected to the communication unit, the other end of the variable capacitance element is connected to the reference potential electrode. The control unit controls the detection unit and the variable capacitance element, the control unit is provided on the substrate and connected to the detection unit and a control terminal of the variable capacitance element. The magnetic field transmitting and receiving unit is separated from the substrate, one end of the magnetic field transmitting and receiving unit is connected to the communication unit and one end of the variable capacitance element, the other end of the magnetic field transmitting and receiving unit is connected to the reference potential electrode. The communication apparatus transmits and receives the signal when a distance between the communication apparatus and a living body is equal to or less than a predetermined distance.

Other embodiments will be described below with reference to the drawings. In the drawings, the same reference signs denote the same or similar portions.

Figure 2:
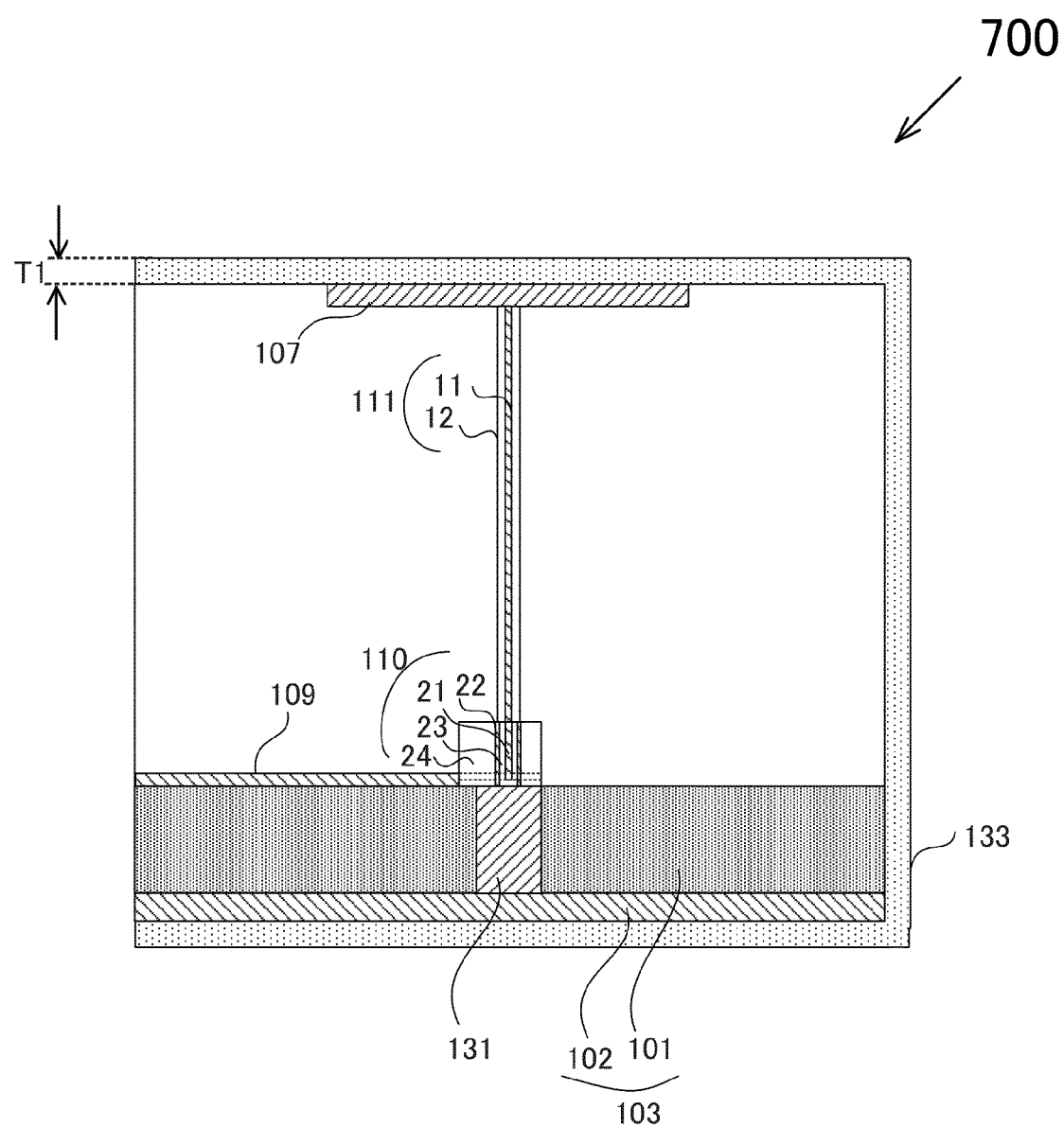
FIG. 2 is a cross-sectional view of the living body detection sensor taken along the A-A line of FIG. 1.
Figure 3:
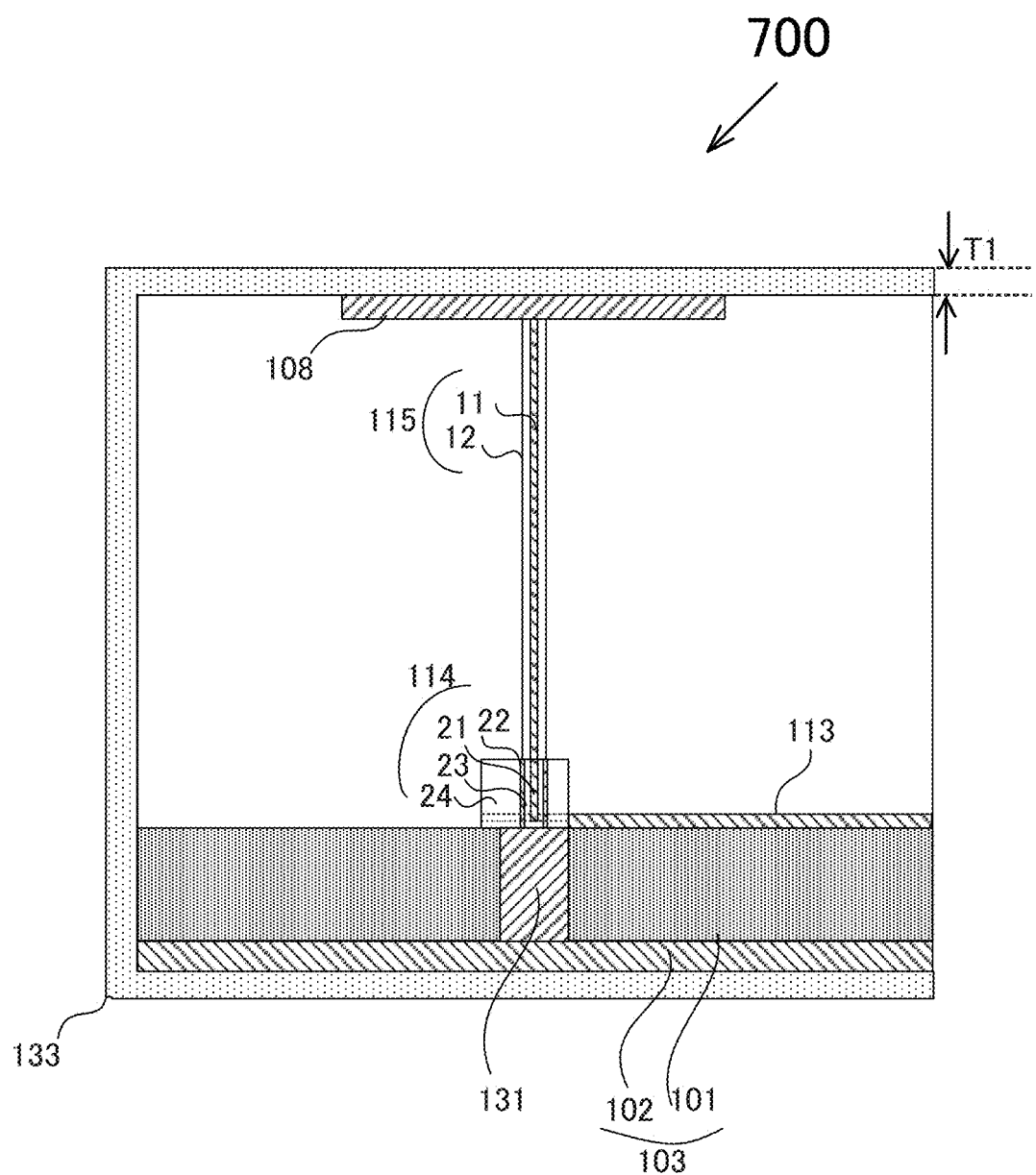
FIG. 3 is a cross-sectional view of the living body detection sensor taken along the B-B line of FIG. 1.

A living body detection sensor of a first embodiment will be described with reference to FIGS. 1, 2, and 3. FIG. 1 is a diagram showing a configuration of the living body detection sensor. FIG. 2 is a cross-sectional view of the living body detection sensor taken along the A-A line of FIG. 1. FIG. 3 is a cross-sectional view of the living body detection sensor taken along the B-B line of FIG. 1. The living body detection sensor of the embodiment recognizes a distance between the living body detection sensor and a human body by use of two conductors opposed to each other, a signal generation unit, a detection unit and a control unit.

As shown in FIG. 1, a living body detection sensor 700 includes a substrate 103, a signal generation unit 104, a detection unit 105, a control unit 106, a conductor 107, a conductor 108, a signal line 109, a signal line 111, a signal line 112, a signal line 113, a signal line 115, a terminal 110, a terminal 114, a via hole 131, a via hole 132 and a housing 133.

The living body detection sensor 700 is configured to make receiving sensitivity lower when a human body as a living body comes close to the living body detection sensor 700, and to detect the presence of the human body when the received signal intensity detected by the detection unit 105 becomes less than a predetermined value. The detail of the configuration will be described later.

The housing 133 is shaped like a box which is larger in the horizontal direction than in the height direction. The housing 133 covers and houses the substrate 103, the signal generation unit 104, the detection unit 105, the control unit 106, the conductor 107, the conductor 108, the signal line 109, the signal line 111, the signal line 112, the signal line 113, the signal line 115, the terminal 110, the terminal 114, the via hole 131 and the via hole 132 inside the housing 133.

In this case, the housing 133 is shaped like a box. Instead, however, the housing 133 may be shaped like a box whose end portions are rounded, or an elliptical sphere.

The substrate 103 is composed of a dielectric material 101 and a reference potential electrode 102. The reference potential electrode 102 is referred to as a ground electrode as well. The dielectric material 101 is provided on a first principal surface (top surface) of the reference potential electrode 102. The dielectric material 101 is made of an insulating ceramic or an insulating organic matter, for example. The reference potential electrode 102 is made of a metal layer of copper (Cu) or gold (Au), for example.

The signal generation unit 104 is provided on a first principal surface (top surface) of the dielectric material 101, and generates a first signal. The terminal 110 (first terminal) is provided on the first principal surface (top surface) of the dielectric material 101, and is connected to the signal generation unit 104 through the signal line 109 (first signal line). The conductor 107 (first conductor) is provided on the first principal surface side of the dielectric material 101, and is connected to the terminal 110 through the signal line (second signal line) 111. The conductor 108 (second conductor) is placed on the first principal surface side of the dielectric material 101, and in parallel with the conductor 107. The conductor 108 is connected to the terminal 114 (second terminal) through the signal line (third signal line) 115.

The conductive bodies 107, 108 are each shaped like a plate. The conductive bodies 107, 108 each function as a signal electrode, and are placed on an upper inner wall of the housing 133. The conductor 107 receives the first signal outputted from the signal generation unit 104, and transmits the first signal to the conductor 108 placed in parallel with the conductor 107. The conductive bodies 107, 108 each use a conductive sheet of copper foil or like, a sintered thin film of conductive ink made by coating or an inkjet method, or a transparent conductive material such as ITO (indium tin oxide), for example.

The terminal 114 is provided on the first principal surface (top surface) of the dielectric material 101, and is connected to the detection unit 105 through the signal line (fourth signal line) 113. The detection unit 105 is provided on the first principal surface (top surface) of the dielectric material 101, and is connected to the control unit 106 through the signal line 112 (6th signal line). The control unit 106 is provided on the first principal surface (top surface) of the dielectric material 101.

The detection unit 105 receives the first signal, outputted from the signal generation unit 104, through the single line 109, the terminal 110, the signal line 111, the conductor 107, the conductor 108, the signal line 115, the terminal 114 and the signal line 113, and detects the signal intensity. The control unit 106 outputs a control signal to the detection unit 105 through the signal line 112, and thus controls the detection unit 105.

As shown in FIG. 2, the signal line 109 is formed on the dielectric material 101. The terminal 110 includes an inner conductor 21, an outer conductor 22, a dielectric material 23 and a dielectric material 24. The inner conductor 21 is provided in the center portion of the terminal 110, and the dielectric material 23 is provided around the inner conductor 21. The outer conductor 22 is provided around the inner conductor 21 with the dielectric material 23 interposed in between. The dielectric material 24 is provided around the outer conductor 22.

The signal line 111 includes an inner signal line 11 and a dielectric material 12. The inner signal line 11 is provided in the center portion of the signal line 111, and the dielectric material 12 is provided around the inner signal line 11. One end of the inner signal line 11 of the signal line 111 is connected to the signal line 109, while the other end of the inner signal line 11 is connected to the signal electrode 107. The signal electrode 107 is provided on the upper inner wall of the housing 133 which has a thickness T1.

As shown in FIG. 3, the signal line 113 is formed on the dielectric material 101. The terminal 114 includes the inner conductor 21, the outer conductor 22, the dielectric material 23 and the dielectric material 24. The inner conductor 21 is provided in the center portion of the terminal 114, and the dielectric material 23 is provided around the inner conductor 21. The outer conductor 22 is provided around the inner conductor 21 with the dielectric material 23 interposed in between. The dielectric material 24 is provided around the outer conductor 22.

The signal line 115 includes the inner signal line 11 and the dielectric material 12. The inner signal line 11 is provided in the center portion of the signal line 115, and the dielectric material 12 is provided around the inner signal line 11. One end of the inner signal line 11 of the signal line 115 is connected to the signal line 113, while the other end of the inner signal line 11 is connected to the signal electrode 108. The signal electrode 108 is provided on the upper inner wall of the housing 133 which has the thickness T1.

Figure 4A:
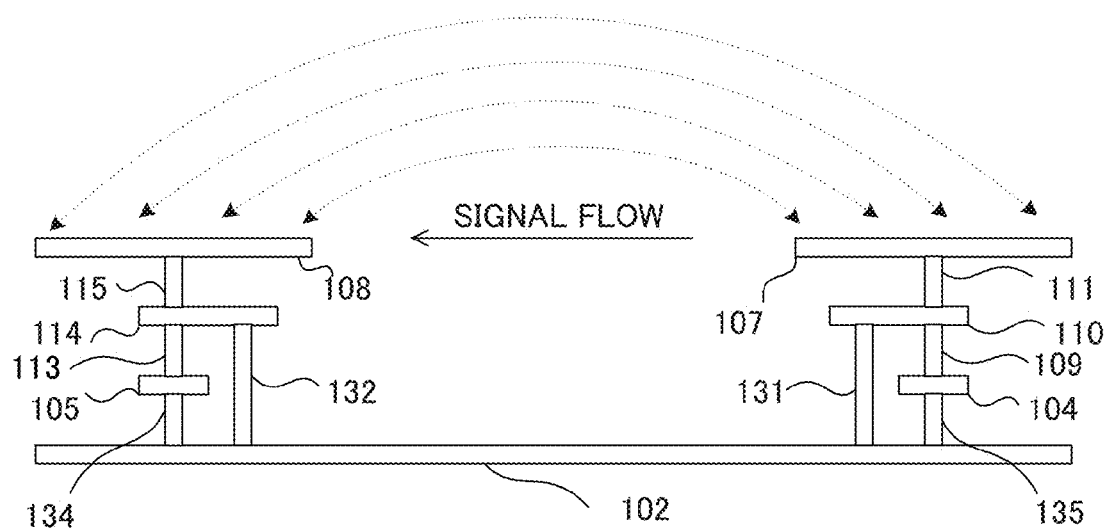
FIGS. 4(A) and 4(B) are diagrams for explaining how the living body detection sensor according to the first embodiment works.
Figure 4B:
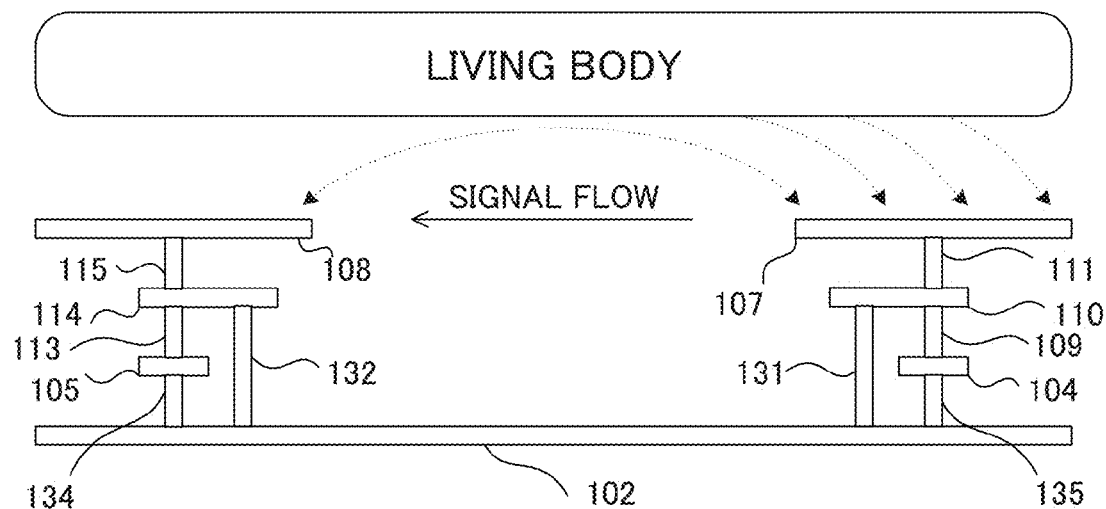

Next, referring to FIGS. 4(A) and 4(B), descriptions will be provided for how the living body detection sensor 700 detects the human body. FIG. 4(A) is a schematic diagram showing how the conductive bodies 107, 108 are spatially coupled to each other. FIG. 4(B) is a schematic diagram showing how the spatial coupling is partially disrupted when the human body comes close to the living body detection sensor 700.

As shown in FIG. 4(A), while the human body is away from the living body detection sensor 700, the conductive bodies 107, 108 are spatially coupled to each other. The first signal outputted from the signal generation unit 104 is inputted into the conductor 108 through the conductor 107, and is detected by the detection unit 105.

As shown in FIG. 4(B), when the human body comes close to the living body detection sensor 700, the spatial coupling occurring between the conductive bodies 107, 108 is partially disrupted by the human body. As a result, the signal intensity of the first signal received by the conductor 108 decreases. This makes it possible for the living body detection sensor 700 to detect whether the human body comes close to the living body detection sensor 700.

Figure 5:
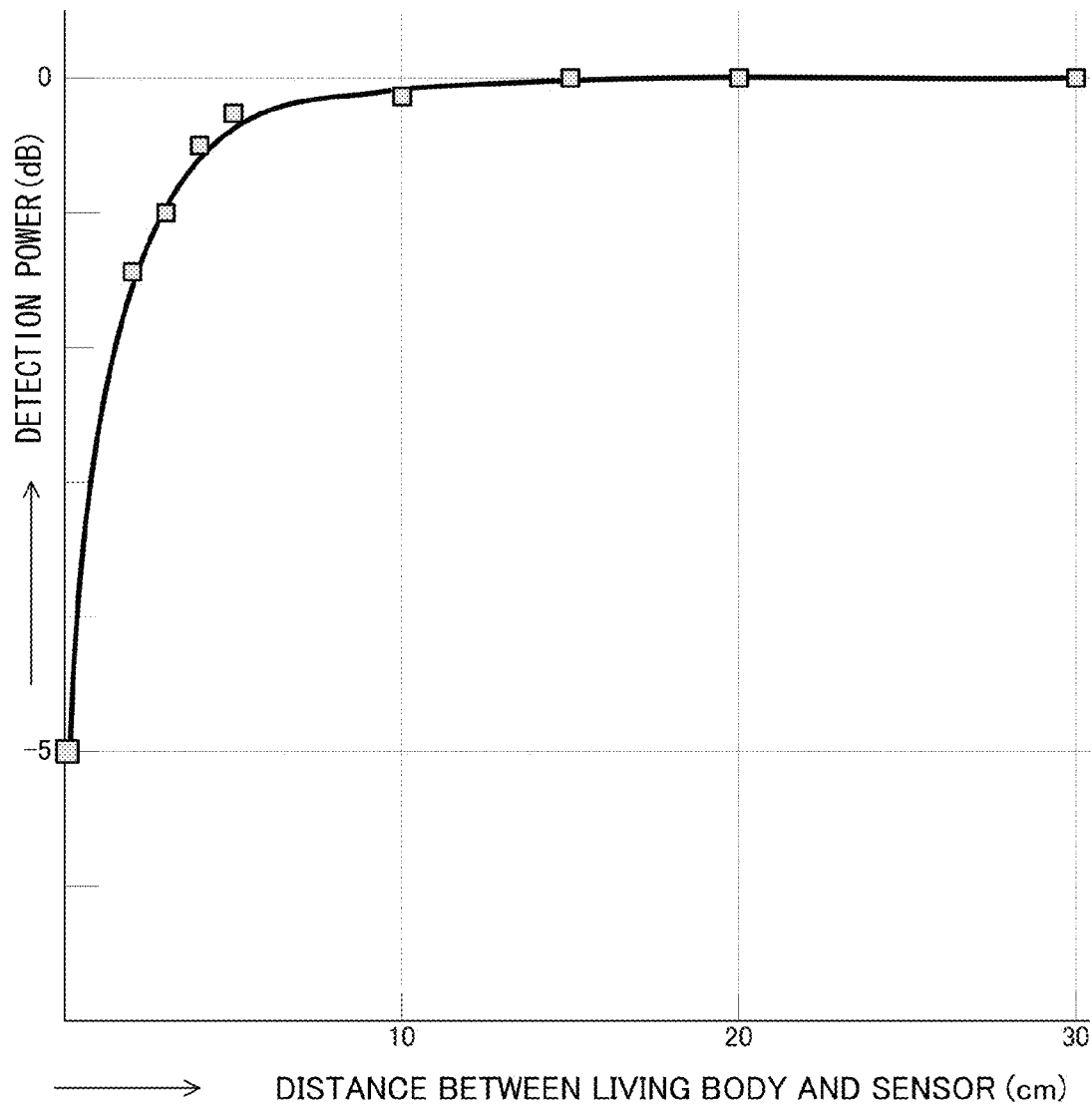
FIG. 5 is a diagram showing a relation of detection power with a distance between a human body and the sensor in the first embodiment.

Next, referring to FIG. 5, descriptions will be provided for a detection characteristic of the living body detection sensor 700. FIG. 5 is a diagram showing a relation of detection power with a distance between the human body and the living body detection sensor 700. In the diagram, the detection power is normalized at 0 (zero) dB when the human body is away from the living body detection sensor 700.

As shown in FIG. 5, while the distance between the human body and the living body detection sensor 700 is equal to or greater than 15 cm, for example, the detection power shows a constant value of 0 (zero) dB. When the distance between the human body and the living body detection sensor 700 decreases to 10 cm, the detection power starts to diminish. When the distance between the human body and the living body detection sensor 700 becomes even shorter, the detection power decreases sharply. When the human body and the living body detection sensor 700 becomes almost equal to 0 (zero), the detection power stands at −5 dB.

The result shows that the living body detection sensor 700 is capable of detecting the approach of the human body with high sensitivity in spite of the relatively simple configuration.

As described above, the living body detection sensor of the embodiment includes the substrate 103, the signal generation unit 104, the detection unit 105, the control unit 106, the conductor 107, the conductor 108, the signal line 109, the signal line 111, the signal line 112, the signal line 113, the signal line 115, the terminal 110, the terminal 114, the via hole 131, the via hole 132 and the housing 133. While the human body is away from the living body detection sensor 700, the conductors 107, 108 are spatially coupled to each other. When the human body comes close to the living body detection sensor 700, the spatial coupling occurring between the conductors 107, 108 becomes partially disrupted by the human body. This resultantly decreases the signal intensity of the first signal received by the conductor 108.

This makes the human body detection sensor 700 capable of detecting the approach of the human body with high sensitivity in spite of the relative simple configuration.

Figure 6:
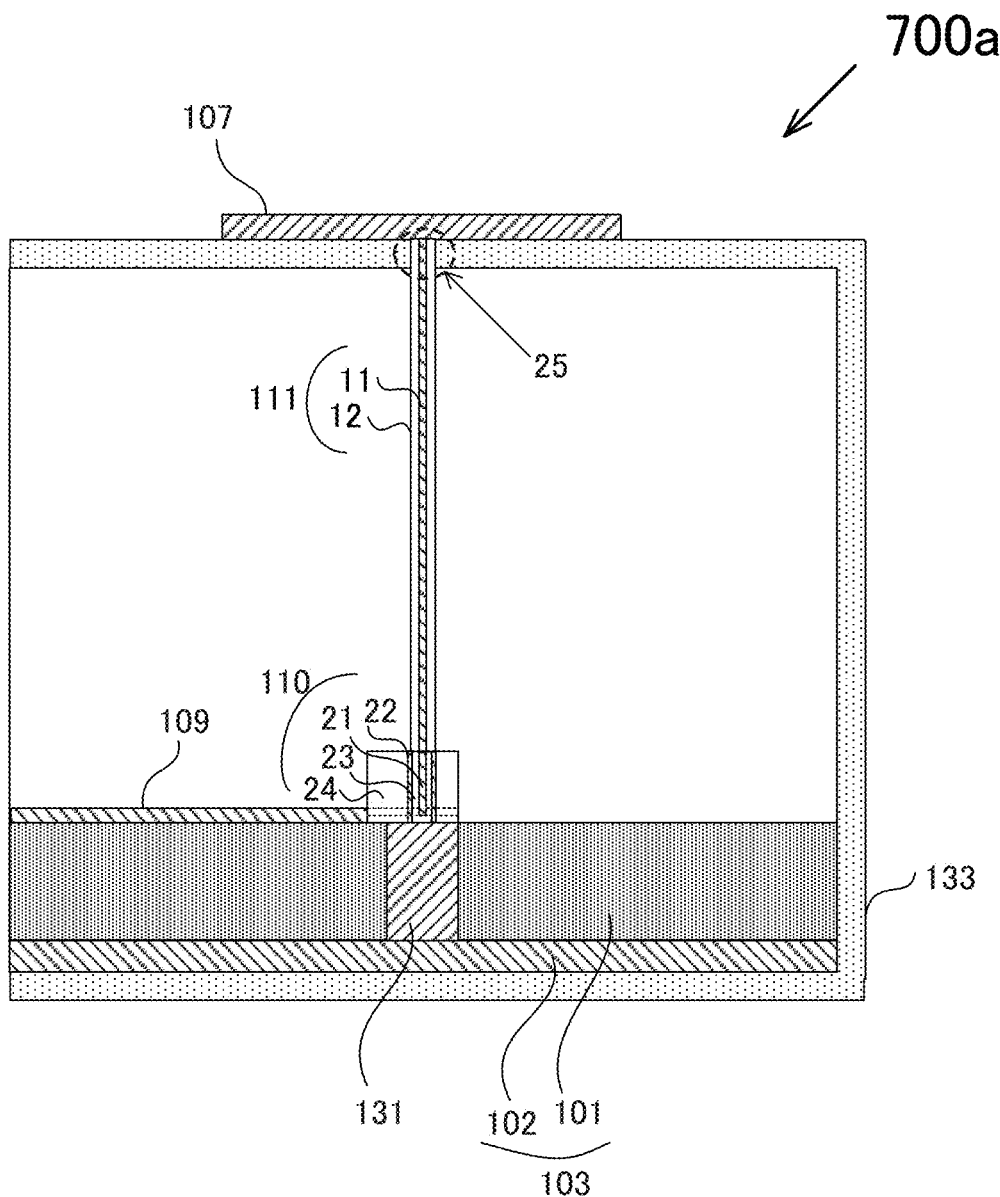
FIG. 6 is a cross-sectional view of a living body detection sensor according to a first modification.

In the embodiment, the conductors 107, 108 are placed on the inner wall of the housing 133. However, the location of the placement is not necessarily limited to this case. For example, the conductors 107, 108 may be placed as in a living body detection sensor 700a of a first modification shown in FIG. 6.

To put it specifically, the conductor 107 may be placed on an outer wall of the housing 133. The conductor 107 is connected to the signal line 111 through a through-hole 25 in the housing 133. Incidentally, it is desirable that albeit not illustrated, the conductor 108 be similarly designed.

Figure 7A:
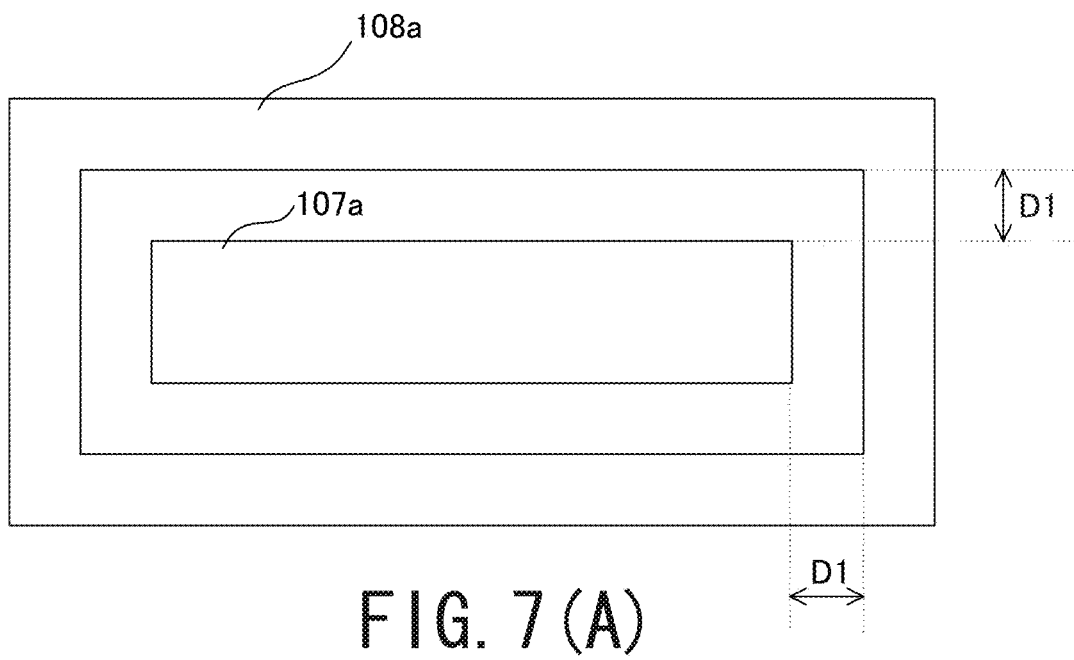
FIGS. 7(A) and 7(B) are cross-sectional views showing living body detection sensors according to a second modification.
Figure 7B:
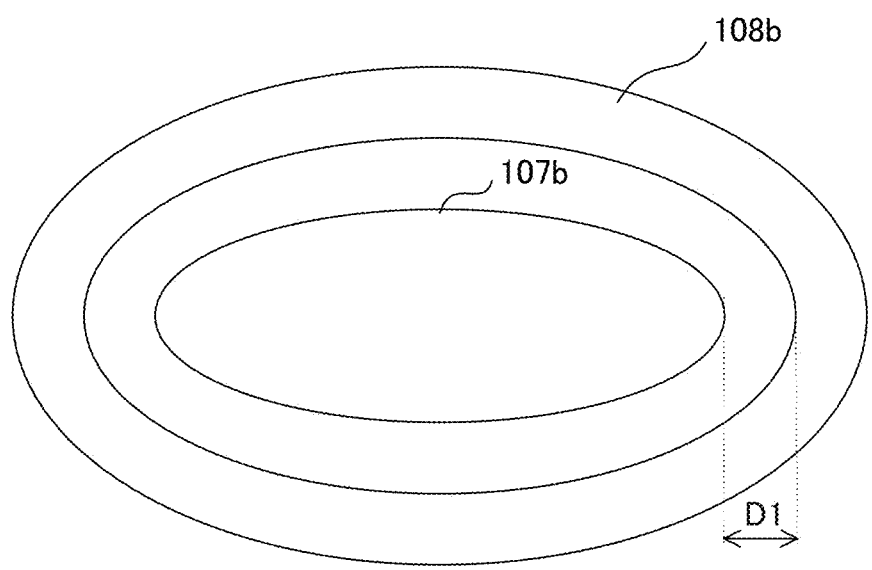

In addition, the shapes and locations of the conductors 107, 108 may be changed as needed. The conductors 107, 108 may be replaced with those having a growth ring structure, for example. To put it specifically, as shown in FIG. 7(A), a conductor 108a having a square-cornered, straight-sided growth ring structure may be placed around a plate-shaped conductor 107a with a distance D1 in between. Alternatively, as shown in FIG. 7(B), a doughnut-shaped conductor 108b may be placed around an elliptic plate-shaped conductor 108a with the distance D1 in between.

The living body detection sensor 700 is provided with the pair of the conductor 107 and the conductor 108. Instead, however, the living body detection sensor 700 may be provided with multiple conductors 107 and multiple conductors 108. In this case, the living body detection sensor is capable of checking the presence of the human body with high sensitivity, no matter what place in the human body the living body detection sensor is close to or in contact with.

In addition, in the embodiment, the signal generation unit 104, the detection unit 105, the control unit 106, the conductor 107, the conductor 108, and the like are provided on the top surface of the substrate 103. However, it is not necessarily limited to this case. For example, the signal generation unit 104, the detection unit 105, the control unit 106, the conductor 107, the conductor 108, and the like may be provided on the back surface or the side surface of the substrate 103.

Figure 8:
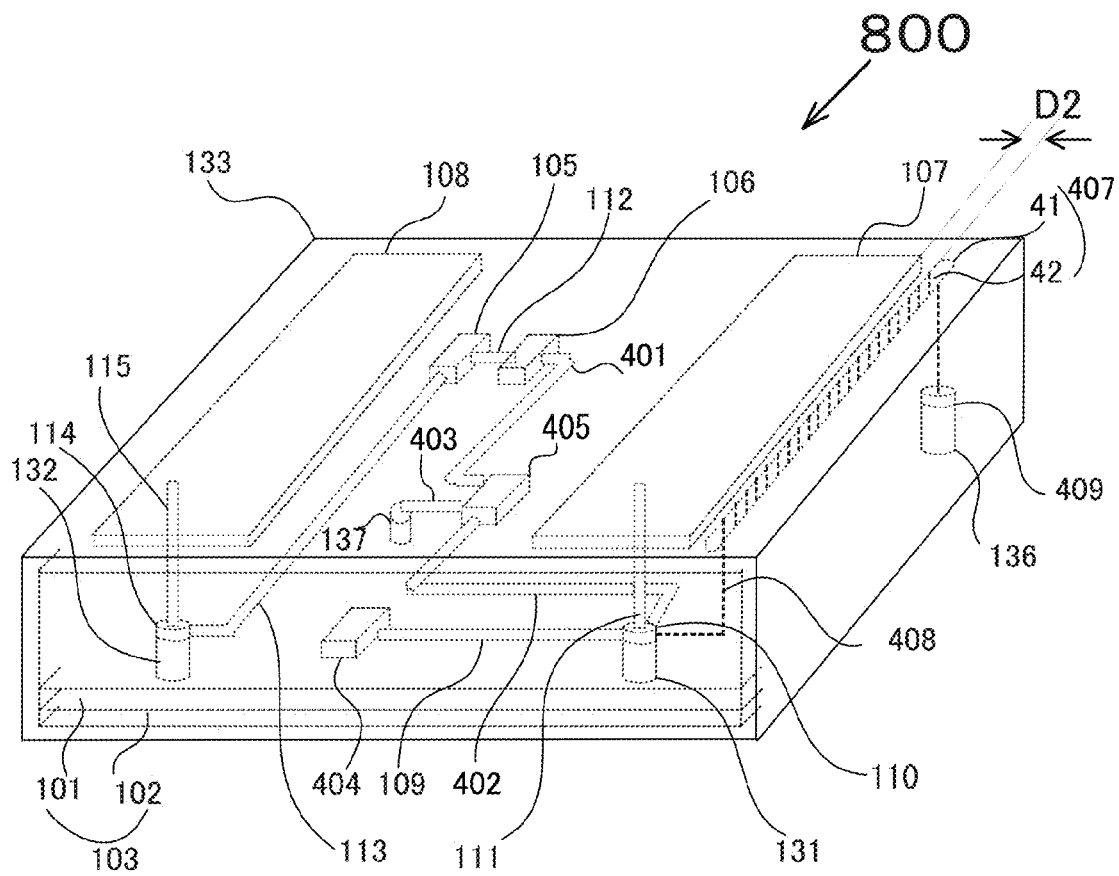
FIG. 8 is a diagram showing a configuration of a communication apparatus according to the second embodiment.
Figure 9:
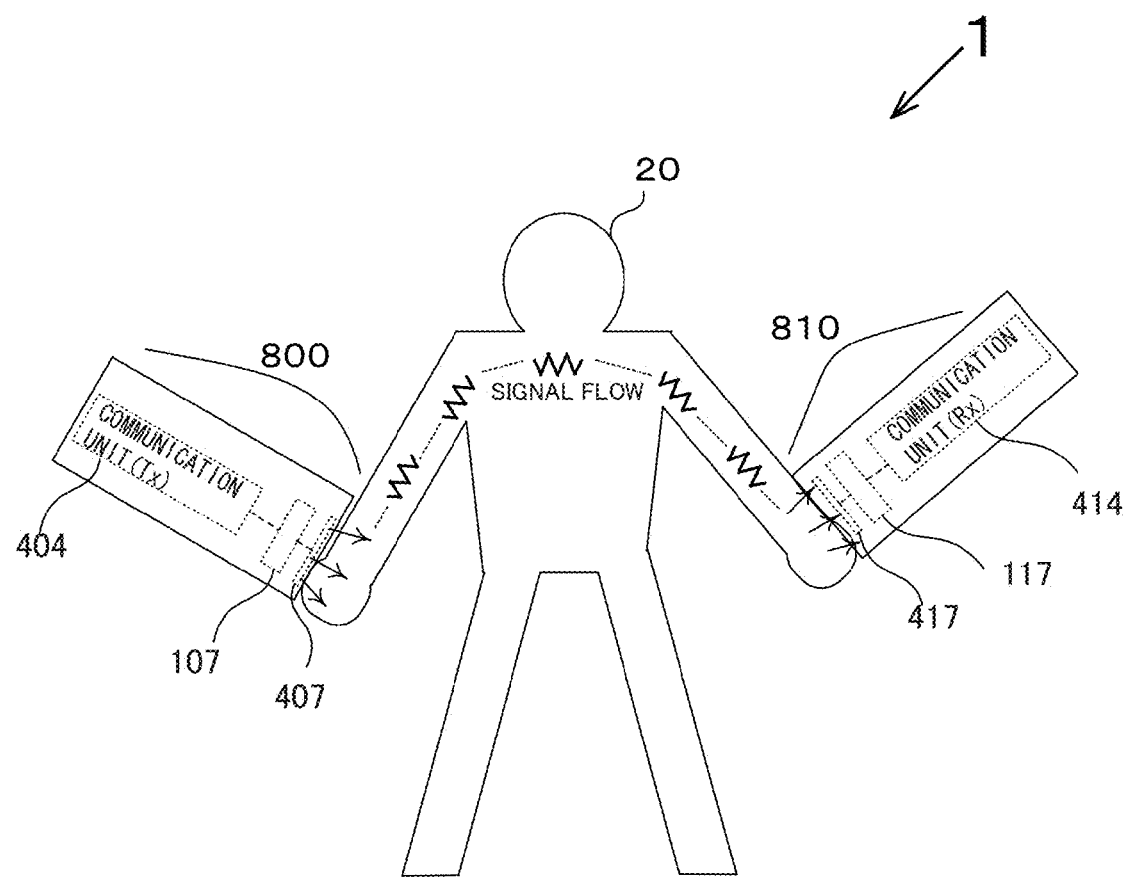
FIG. 9 is a diagram showing a configuration of a communication system according to the second embodiment.
Figure 10:
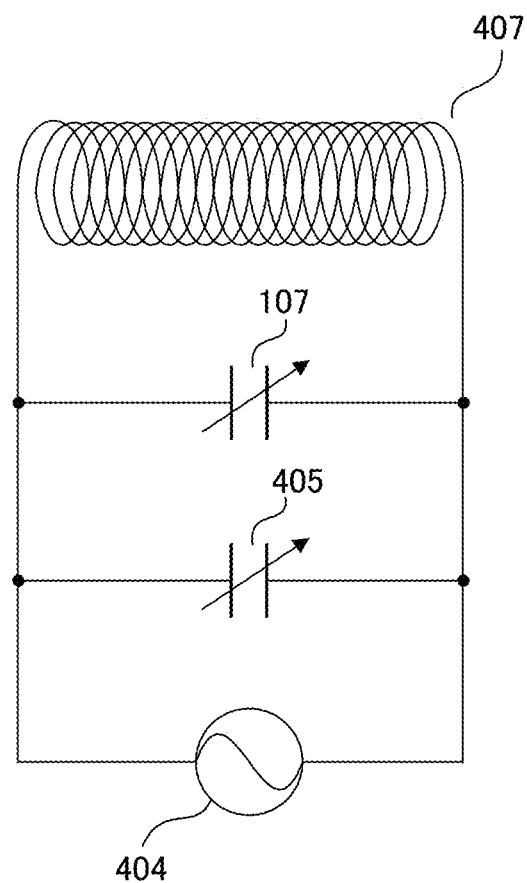
FIG. 10 is an equivalent circuit diagram of the communication apparatus according to the second embodiment.

A communication apparatus of a second embodiment will be described with reference to FIGS. 8, 9, and 10. FIG. 8 is a diagram showing a configuration of the communication apparatus. FIG. 9 is a diagram showing a configuration of a communication system. FIG. 10 is an equivalent circuit diagram of the communication apparatus. The communication apparatus of the second embodiment includes the living body detection sensor of the first embodiment as a component, and is designed to be communicable only when the human body is within a predetermined distance from the communication apparatus.

In the following, component portions which are the same as those of the first embodiment will be denoted by the same reference signs. Descriptions for such portions will be omitted, and descriptions will be provided for different portions only.

As shown in FIG. 8, a communication apparatus 800 includes a substrate 103, a detection unit 105, a control unit 106, a conductor 107, a conductor 108, a signal line 109, a signal line 111, a signal line 112, a signal line 113, a signal line 115, a terminal 110, a terminal 114, a via hole 131, a via hole 132, a housing 133, a via hole 136, a via hole 137, a signal line 401, a signal line 402, a signal line 403, a signal line 408, a communication unit 404, a variable capacitance element 405 and a magnetic field transmitting and receiving unit 407.

The communication apparatus 800 is different from the living body detection sensor 700 of the first embodiment in that the signal generation unit 104 is replaced with the communication unit 404, and in that the via hole 136, the via hole 137, the signal line 401, the signal line 402, the signal line 403, the signal 408, the variable capacitance element 405 and the magnetic field transmitting and receiving unit 407 are added to the living body detection sensor 700. The communication apparatus 800 is designed to be communicable only when the human body is within the predetermined distance from the communication apparatus 800. Details of the communication apparatus 800 will be described later.

The housing 133 is shaped like a box which is larger in the horizontal direction than in the height direction. The housing 133 covers and houses the substrate 103, the detection unit 105, the control unit 106, the conductor 107, the conductor 108, the signal line 109, the signal line 111, the signal line 112, the signal line 113, the signal line 115, the terminal 110, the terminal 114, the via hole 131, the via hole 132, the via hole 136, the via hole 137, the signal line 401, the signal line 402, the signal line 403, the signal line 408, the communication unit 404, the variable capacitance element 405 and the magnetic transmitting and receiving unit 407 inside the housing 133.

The communication unit 404 is provided on the first principal surface (top surface) of the dielectric material 101, and sends and receives data. Although not illustrated, the ground electrode of the communication unit 404 is connected to the reference potential electrode 102 through a via hole. The communication unit 404 is connected to the terminal 110 through the signal line 109 (first signal line).

The variable capacitance element 405 is provided on the first principal surface (top surface) of the dielectric material 101, and is connected to the terminal 110 through the signal line (fifth signal line) 402. The ground portion (not illustrated) of the variable capacitance element 405 is connected to the reference potential electrode 102 through the via hole 137. The control terminal (not illustrated) of the variable capacitance element 405 is connected to the control unit 106 through the signal line (7th signal line) 401. The variable capacitance element 405 makes the capacitance variable on the basis of a control signal outputted from the control unit 106 through the signal line (7th signal line) 401.

The variable capacitance element 405 is formed from a MEMS-type variable capacitance element or a variable capacitance diode.

The magnetic field transmitting and receiving unit 407 is placed on the side near the first principal surface of the dielectric material 101 while spaced out from the conductor 107 with a distance D2 in between. The magnetic field transmitting and receiving unit 407 includes a signal line 42 spirally wound around a magnetic material 41 and a magnetic material 41. The magnetic material 41 is referred to as a ferrite bar as well. One end of the signal line 42 is connected to the terminal 110 through the signal line 408 (8th signal line) and the other end of the signal line 42 is connected to a terminal 409 through a signal line.

The terminal 409 is provided on the first principal surface (top surface) of the dielectric material 101, and is connected to the reference potential electrode 102 through the via hole 136.

As shown in FIG. 9, the communication system 1 includes the communication apparatus 800 and a communication apparatus 810. The communication system 1 performs wearable computing/communication between the communication apparatus 800 and the communication apparatus 810 through a living body 20 such as a human body. The communication system 1 performs short-range wireless communication through the living body 20.

In the communication system 1, when the communication unit 404 of the communication apparatus 800 serves as a transmission unit (TX), for example, data transmitted from the communication unit 404 are transferred to a communication unit 414 of the communication apparatus 810 through the conductor 107, the magnetic field transmitting and receiving unit 407, the human body 20, a magnetic field transmitting and receiving unit 417 of the communication apparatus 810 and a conductor 117 of the communication apparatus 810. In this case, the communication unit 414 serves as a reception unit (Rx). On the other hand, when the communication unit 414 of the communication apparatus 810 serves as the transmission unit (Tx), the communication unit 404 of the communication apparatus 800 serves as the reception unit 404 (Rx).

In the communication apparatus 800, the communication unit 404, the variable capacitance element 405, the conductor 107 and the magnetic field transmitting and receiving unit 407 jointly form the same configuration as an equivalent circuit of a bar antenna, as shown in FIG. 10. The conductor 107 and the variable capacitance element 405 jointly function as a matching adjustment element of the bar antenna. The capacitance of the conductor 107 varies in accordance with the distance between the conductor 107 and the human body 20. Although not illustrated, the communication apparatus 810 has the same configuration as the communication apparatus 800.

Figure 11:
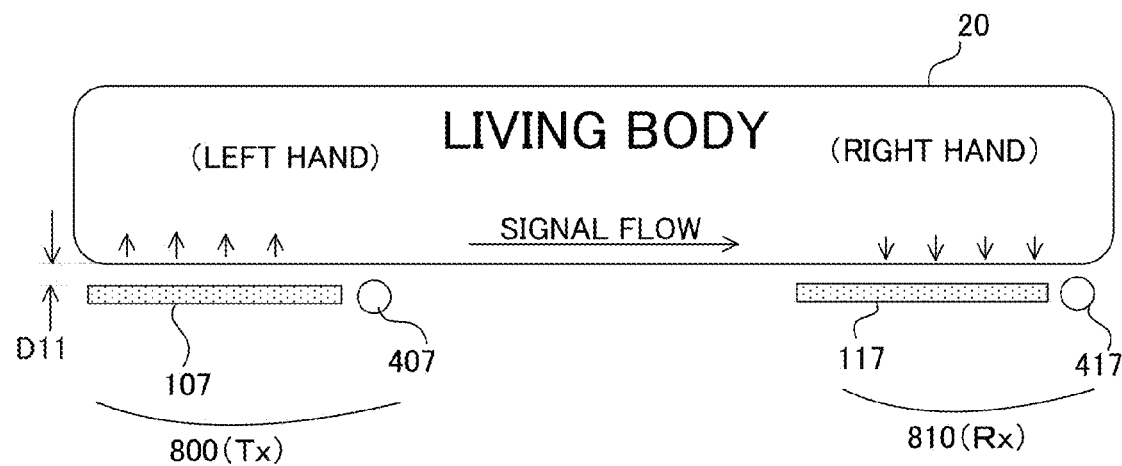
FIGS. 11(A) and 11(B) are diagrams for explaining how the communication apparatus of the second embodiment makes a judgment about transmission and reception.
Figure 11:
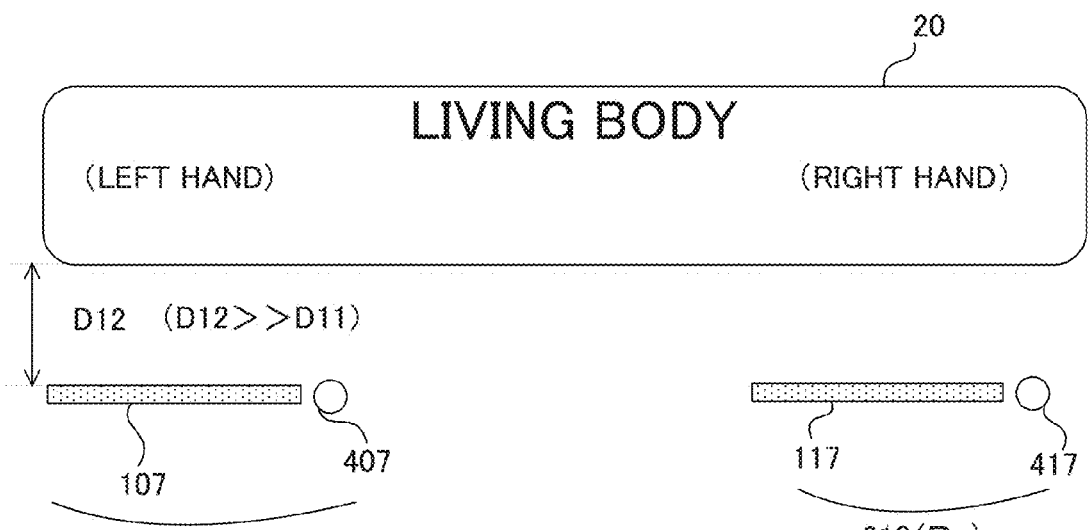

Next, referring to FIGS. 11(A) and 11(B), descriptions will be provided for how the communication apparatuses make a determination about the transmission and reception. In this case, let us assume that the communication apparatus 800 provides the transmission unit (Tx) while the communication apparatus 810 provides the reception unit (Rx). FIG. 11(A) shows a case where the human body 20 is close to the communication apparatus 800(Tx) and the communication apparatus 810(Rx). FIG. 11(B) shows a case where the human body 20 is away from the communication apparatus 800(Tx) and the communication apparatus 810(Rx) by a predetermined distance or more.

As shown in FIG. 11(A), when the human body 20 is away from the communication apparatus 800(Tx) and the communication apparatus 810(Rx) by a distance D11 which is shorter than the predetermined distance, the detection unit 105 of the living body detection sensor detects the human body 20, and the control unit 106 controls the capacitance of the variable capacitance element 405 in order that the variable capacitance element 405 can have predetermined capacitance. Thereby, the bar antenna becomes capable of performing the matching adjustment and thus communicable only when the human body 20 is close to the communication apparatus 800(Tx) and the communication apparatus 810 (Tx). As a result, a signal outputted from the communication unit 404 of the communication apparatus 800 is inputted into the communication unit 414 of the communication apparatus 810.

On the other hand, as shown in FIG. 11(B), when the human body 20 is away from the communication apparatus 800(Tx) and the communication apparatus 810(Rx) by a distance D12 which is longer than the predetermined distance, the detection unit 105 of the living body detection sensor does not detect the human body 20, and the control unit 106 does not control the variable capacitance element 405. For this reason, the matching adjustment of the bar antenna does not function, and accordingly, no communication can be carried out between the communication apparatus 800 and the communication apparatus 810.

Figure 12:
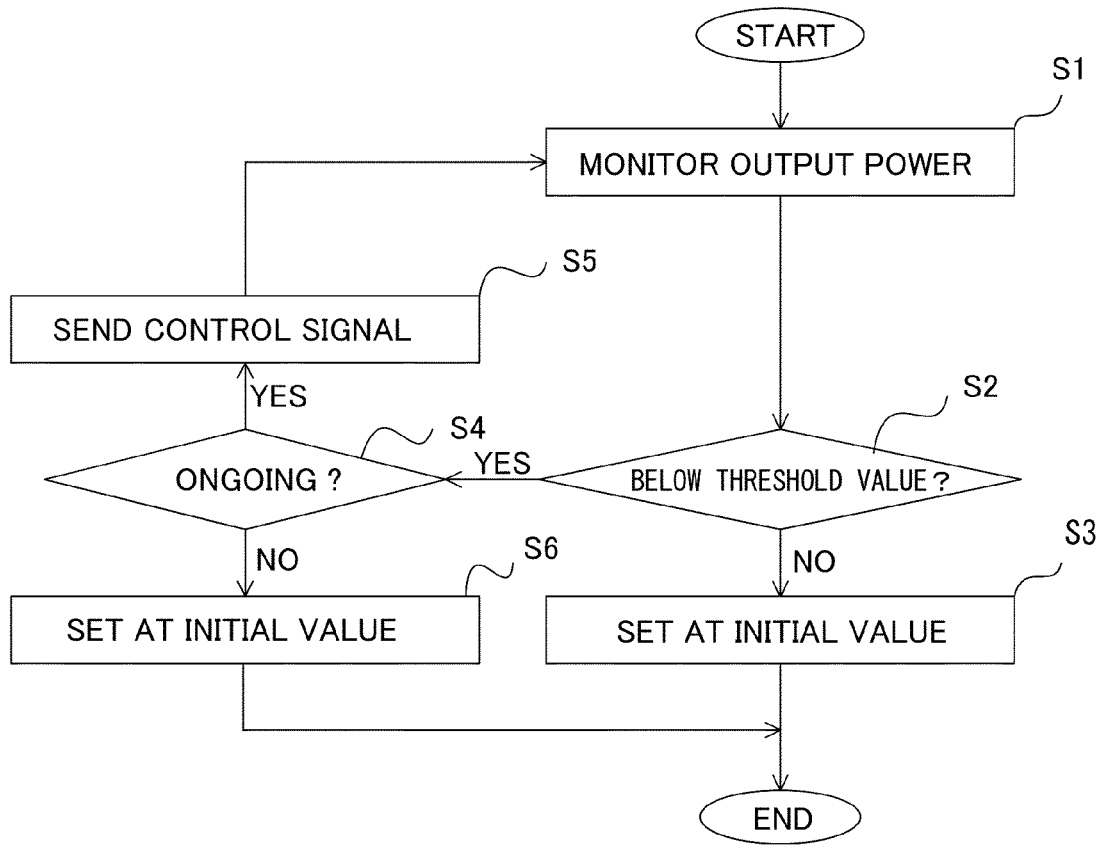
FIG. 12 is a flowchart showing an operation of the communication apparatus according to the second embodiment.

Next, referring to FIG. 12, descriptions will be provided for how the communication apparatuses work. FIG. 12 is a flowchart showing how the communication apparatus 800 works from the start to end of the communication.

As shown in FIG. 12, once the communication starts, a transmission signal (hereinafter referred to as a second signal) is inputted into the conductor 107 and the magnetic field transmitting and receiving unit 407 from the communication unit 404. The second signal inputted into the conductor 107 is received by the conductor 108 which is spatially coupled to the conductor 107, and is detected by the detection unit 105. The result of the detection (the value of the detection power of the second signal) is monitored by the control unit 106 (step S1).

The control unit 106 determines whether or not the value of the detection power of the second signal is below a threshold value (a value corresponding to the predetermined distance of the human body 20 from the living body detection sensor), that is to say, whether or not the human body 20 is close to the communication apparatus 800 (step S2).

When the control unit 106 determines that no human body is close to the communication apparatus 800, the control unit 106 controls the variable capacitance element 405 so that the value of the variable capacitance element 405 can be set at an initial value (step S3). As a result, the communication is terminated at this point of time.

When the control unit 106 determines that the human body is close to the communication apparatus 800, the control unit 106 determines whether or not the communication is ongoing (step S4).

When the control unit 106 determines that the communication is ongoing, the control unit 106 sends the variable capacitance element 405 a control signal corresponding to the output value (step S5).

When the control unit 106 determines that no communication is ongoing, the control unit 106 controls the variable capacitance element 405 so that the value of the variable capacitance element 405 can be set at the initial value (step S6). As a result, the communication is terminated at this point of time.

It should be noted that during the communication, the control unit 106 always monitors the value of the detection power of the second signal detected by the detection unit 105, and continues controlling the variable capacitance element 405 in accordance with the output value.

As described above, each communication apparatus of the embodiment includes the substrate 103, the detection unit 105, the control unit 106, the conductor 107, the conductor 108, the signal line 109, the signal line 111, the signal line 112, the signal line 113, the signal line 115, the terminal 110, the terminal 114, the via hole 131, the via hole 132, the housing 133, the via hole 136, the via hole 137, the signal line 401, the signal line 402, the signal line 403, the signal line 408, the communication unit 404, the variable capacitance element 405 and the magnetic field transmitting and receiving unit 407. The control unit 106 controls the variable capacitance element 405 in accordance with the output value from the living body detection sensor.

Thereby, the communication apparatus 800 is capable of performing communication only while the human body 20 is close to the communication apparatus 800 within the predetermined distance.

In addition, in the embodiment, the detection unit 105, the control unit 106, the conductor 107, the conductor 108, the communication unit 404, the variable capacitance element 405 and the magnetic transmitting, receiving unit 407, and the like are provided on the top surface of the substrate 103. However, it is not necessarily limited to this case. For example, the detection unit 105, the control unit 106, the conductor 107, the conductor 108, the communication unit 404, the variable capacitance element 405 and the magnetic transmitting, receiving unit 407, and the like may be provided on the back surface or the side surface of the substrate 103.

Figure 13:
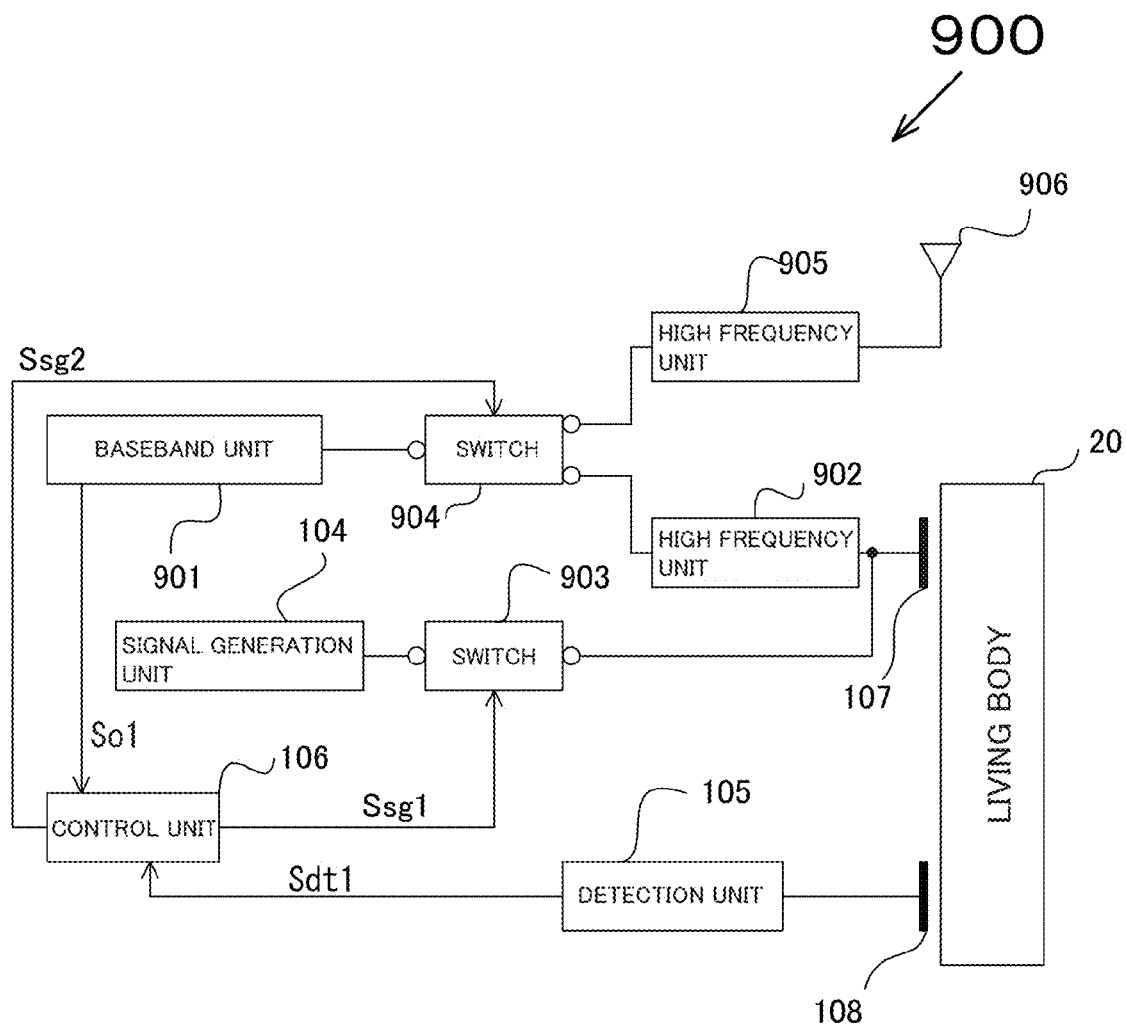
FIG. 13 is a block diagram showing a configuration of a communication apparatus according to a third embodiment.

A living body detection sensor of a third embodiment will be described with reference to FIG. 13. FIG. 13 is a block diagram showing a configuration of the living body detection sensor including a communication function. In the embodiment, communication is performed employing an electromagnetic field produced around a human body while the human body is close to the living body detection sensor, and employing an antenna while the human body is away from the living body detection sensor.

In the following, component portions which are the same as those of the first embodiment will be denoted by the same reference signs. Descriptions for such portions will be omitted, and descriptions will be provided for different portions only.

As shown in FIG. 13, a living body detection sensor 900 has the communication function. The living body detection sensor 900 includes a signal generation unit 104, a detection unit 105, a control unit 106, a conductor 107, a conductor 108, a baseband unit 901, a high frequency unit 902, a switch 903, a switch 904, a high frequency unit 905 and an antenna 906.

In this respect, the signal generation unit 104, the detection unit 105, the control unit 106, the conductor 107 and the conductor 108 perform the same operations as those of the living body detection sensor 700 of the first embodiment. A detection signal Sdt1 detected by the detection unit 105 is sent to the control unit 106. To put it specifically, as the human body 20 comes close to the living body detection sensor, the reception sensitivity becomes lower. Once the received signal intensity detected by the detection unit 105 becomes equal to or less than a predetermined value, the detection unit 105 detects the presence of the human body 20.

The signal generation unit 104 outputs a first signal to the switch 903. The switch 903 is provided between the signal generation unit 104 and the conductor 107. The switch 903 connects the signal generation unit 104 and the conductor 107 together on the basis of a control signal Ssg1 in an enable state outputted from the control unit 106. The switch 903 is a SPST switch.

The baseband unit 901 outputs a signal So1 to the control unit 106. The baseband unit 901 sends and receives a signal to and from the switch 904. The switch 904 is provided between the baseband unit 901 and the pair of the high frequency units 902, 905. The switch 904 connects the baseband unit 901 and the high frequency unit 902 together, or the baseband unit 901 and the high frequency unit 905 together, on the basis of a control signal Ssg2 outputted from the control unit 106. The switch 904 is a SPDT switch.

The high frequency unit 902 is provided between the switch 904 and the conductor 107. The high frequency unit 905 is provided between the switch 904 and the antenna 906.

Figure 14:
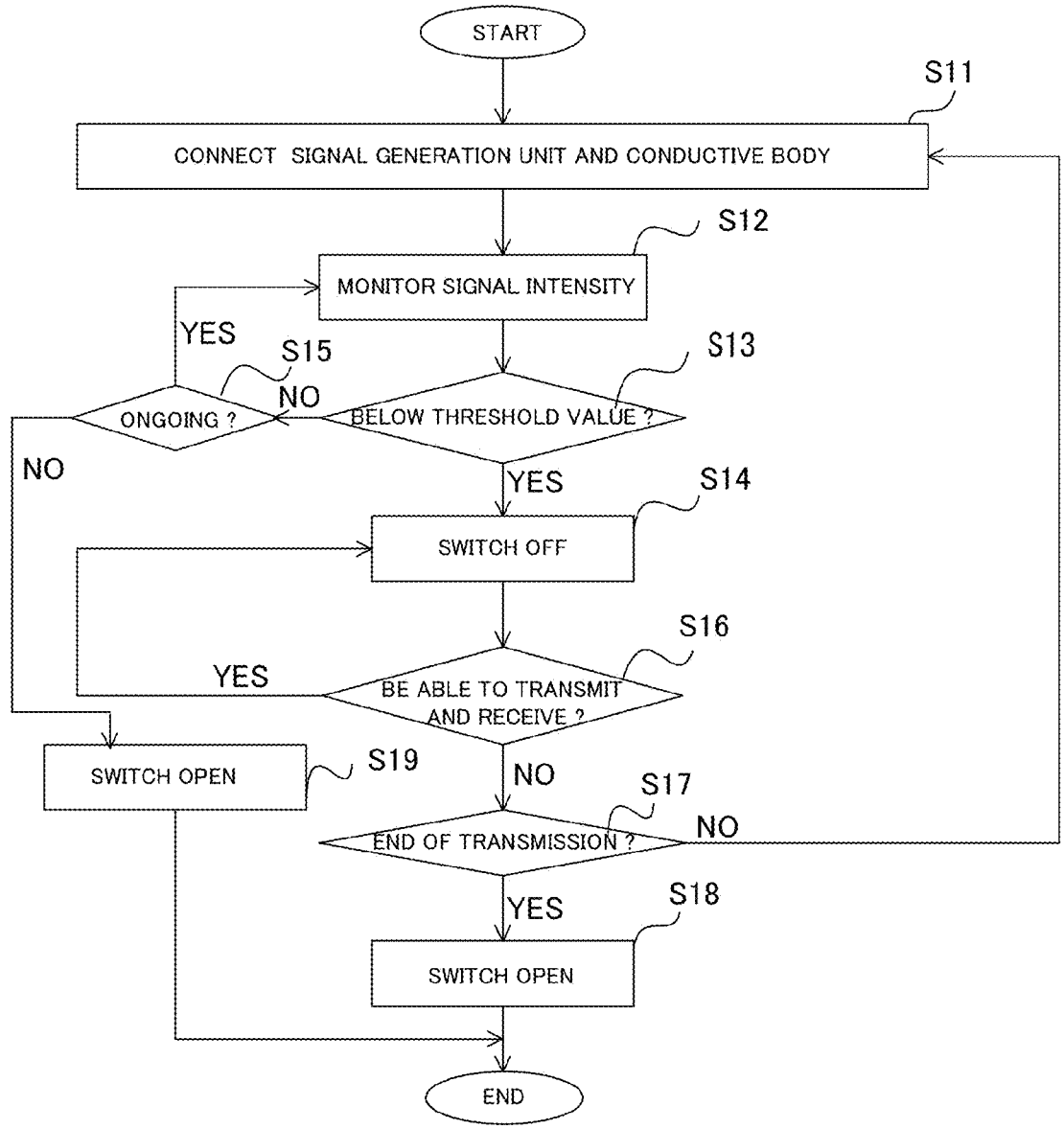
FIG. 14 is a flowchart showing an operation of a living body detection sensor having a communication function according to the third embodiment.
Figure 15:
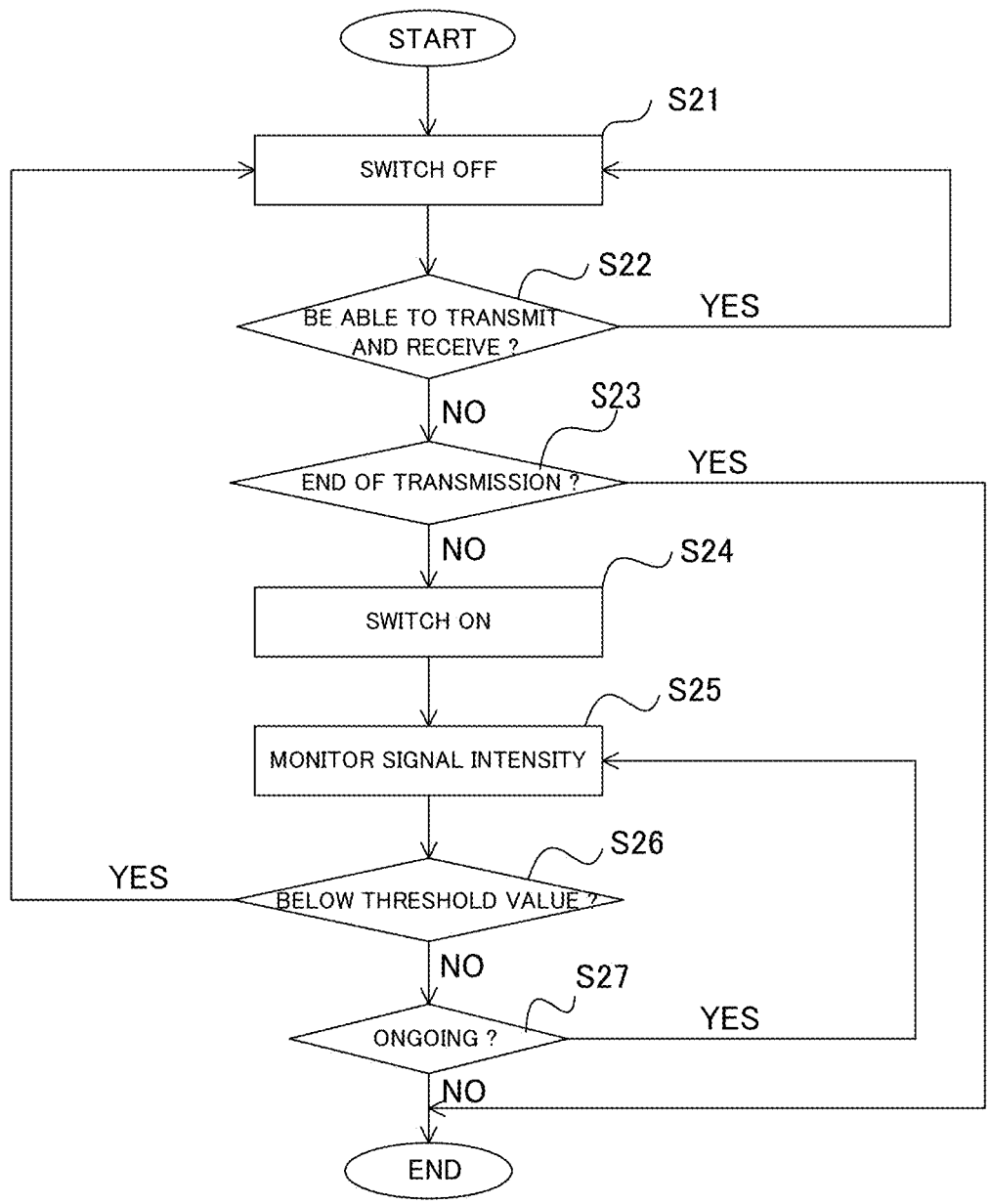
FIG. 15 is another flowchart showing an operation of the living body detection sensor having the communication function according to the third embodiment.

Next, referring to FIGS. 14 and 15, descriptions will be provided for how the living body detection sensor having the communication function works. FIGS. 14 and 15 are flowcharts showing an operation of the living body detection sensor having the communication function.

FIG. 14 is the flowchart for a case where the high frequency unit 905 is selected at the beginning of the communication. As shown in FIG. 14, once the communication starts, the signal So1 to start the communication is sent from the baseband unit 901 to the control unit 106. The control unit 106 sends the switch 904 the control signal Ssg2 to connect the baseband unit 901 and the high frequency unit 905 together. As a result, the communication starts by employing the antenna 906. Simultaneously, the control unit 106 sends the switch 903 the control signal Ssg1 in the enable state to connect the signal generation unit 104 and the conductor 107 together. Thereby, the human body 20 is detected using the conductors 107 and 108 (step S11).

While the communication is being performed employing the antenna 906, the control unit 106 is monitoring the signal intensity detected by the detection unit 105 (step S12).

The control unit 106 determines whether or not the detection power value is below the threshold value (the value corresponding to the predetermined distance of the human body 20 from the living body detection sensor), that is to say, whether or not the human body 20 is close to the living body detection sensor (step S13).

When the control unit 106 determines that the detection power value is equal to or less than the threshold value, the control unit 106 sends the switch 904 the control signal Ssg2 to connect the baseband unit 901 and the high frequency unit 902 together. Simultaneously, the control unit 106 sends the switch 903 the control signal Ssg1 in a disable state to disconnect the signal generation unit 104 and the conductor 107 from each other (step S14). As a result, the control unit 106 uses the conductor 107 to perform switching to the communication employing the electromagnetic field produced around the human body 20.

When the control unit 106 determines that the detection power value is equal to or greater than the threshold value, the control unit 106 determines whether or not the communication is ongoing (step S15). When the control 106 determines that the communication is ongoing, the control unit 106 monitors the signal intensity detected by the detection unit 105.

When the control unit 106 determines that no communication is ongoing, the control unit 106 sends the switch 903 the control signal Ssg1 in the disable state to disconnect the signal generation unit 104 and the conductor 107 from each other (step S19). Thereby, the communication is terminated.

After the control unit 106 performs the switching to the communication employing the electromagnetic field, the control unit 106 determines whether or not the transmission and reception operation employing the electromagnetic field is established (step S16). When the control unit 106 determines that the transmission and reception operation employing the electromagnetic field is established, the control unit 106 continues with the communication employing the electromagnetic field.

When it is determined that the transmission and reception operation employing the electromagnetic field is not established, the control unit 106 determines whether or not to terminate the transmission (step S17).

FIG. 15 is the flowchart for a case where the high frequency unit 902 is selected at the beginning of the communication. As shown in FIG. 15, once the communication starts, the signal So1 to start the communication is sent from the baseband unit 901 to the control unit 106. The control unit 106 sends the switch 904 the control signal Ssg2 to connect the baseband unit 901 and the high frequency unit 902 together. Simultaneously, the control unit 106 sends the switch 903 the control signal Ssg1 in the enable state to connect the signal generation unit 104 and the conductor 107 together. This starts the detection of the human body 20 using the conductors 107, 108. When the control unit 106 determines that the human body 20 is close to the living body detection sensor by the predetermined distance or less, the control unit 106 sends the switch 903 the control signal Ssg1 in the disable state to disconnect the signal generation unit 104 and the conductor 107 from each other. As a result, the communication employing the electromagnetic field produced around the human body 20 is performed by use of the conductor 107 (step S21).

The control unit 106 determines whether or not the transmission and reception operation for the communication employing the electromagnetic field is established (step S22). When the control unit 106 determines that the transmission and reception operation employing the electromagnetic field is established, the control unit 106 continues with the communication employing the electromagnetic field.

When the control unit 106 determines that the transmission and reception operation for the communication employing the electromagnetic field is not established, the control unit 106 judges whether or not to terminate the communication (step S23). When the control unit 106 determines that the communication should be terminated, the control unit 106 brings the communication to an end.

When the control unit 106 determines that the communication should not be terminated, the control unit 106 sends the switch 904 the control signal Ssg2 to connect the baseband unit 901 and the high frequency unit 905 together. Simultaneously, the control unit 106 sends the switch 903 the control signal Ssg1 in the enable state to connect the signal generation unit 104 and the conductor 107 together. This starts the detection of the human body 20 using the conductors 107, 108.

While the communication is being performed employing the antenna 906, the control unit 106 is monitoring the signal intensity detected by the detection unit 105 (step S25).

The control unit 106 determines whether or not the detection power value is below the threshold value (the value corresponding to the predetermined distance of the human body 20 from the living body detection sensor), that is to say, whether or not the human body 20 is close to the living body detection sensor (step S26).

When the control unit 106 determines that the detection power value is equal to or less than the threshold value, the procedure returns to step S21. When the control unit 106 determines that the detection power value is equal to or greater than the threshold value, the control unit 106 judges whether or not the communication is ongoing (step S27). When the control unit 106 determines that the communication is ongoing, the procedure returns to step S25. When the control unit 106 determines that the communication is no longer ongoing, the control unit 106 terminates the communication operation.

As described above, the living body detection sensor of the embodiment includes the signal generation unit 104, the detection unit 105, the control unit 106, the conductor 107, the conductor 108, the baseband unit 901, the high frequency unit 902, the switch 903, the switch 904, the high frequency unit 905 and the antenna 906. The signal generation unit 104, the detection unit 105, the control unit 106, the conductor 107 and the conductor 108 jointly function as the living body detection sensor. When the human body 20 is away from the living body detection sensor by the predetermined distance or more, the switch 904 connects the baseband unit 901 and the high frequency unit 905 together under control of the control unit 106. When the human body 20 is close to the living body detection sensor by the predetermined distance or less, the switch 903 disconnects the signal generation unit 104 and the conductor 107 from each other, and the switch 904 connects the baseband unit 901 and the high frequency unit 902 together, under control of the control unit 106.

This enables the living body detection sensor 900 having the communication function to perform the communication employing the electromagnetic field produced around the human body 20 when the human body 20 is close to the living body detection sensor 900 by the predetermined distance or less, and the communication employing the antenna when the human body 20 is away from the living body detection sensor by the predetermined distance or more.

The living body detection sensor 900 having the communication function performs the communication employing the electromagnetic field produced around the human body 20 by use of the conductor 107. However, the use of the conductor 107 is not necessarily the only way for the living body detection sensor 900 to perform the communication. The living body detection sensor 900 may perform the communication by use of the magnetic field transmitting and receiving unit 407 of the second embodiment connected to the high frequency unit 902, for example.

Figure 16:
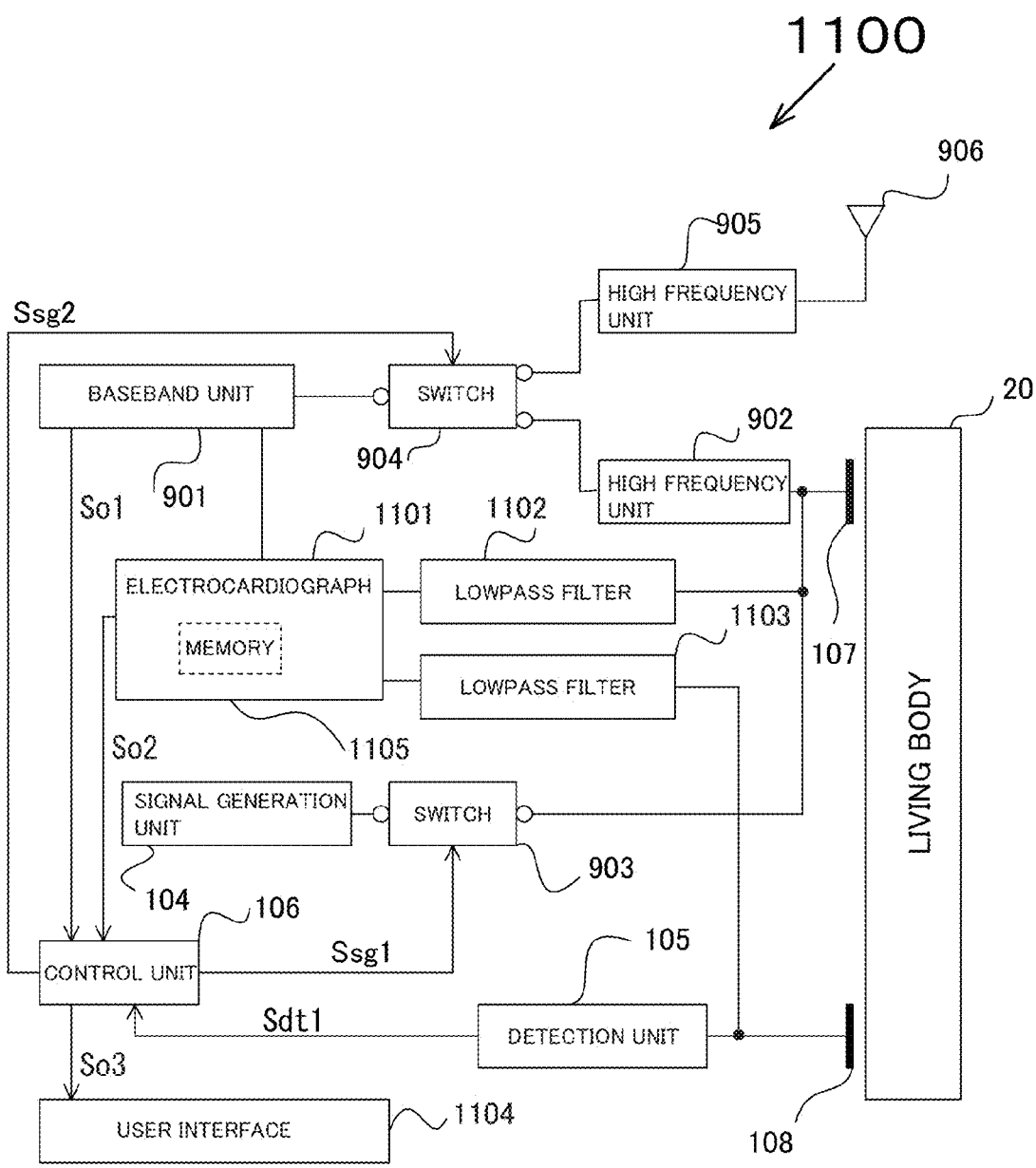
FIG. 16 is a block diagram showing a configuration of a living body detection sensor having a communication function according to a fourth embodiment.

A living body detection sensor of a fourth embodiment will be described with reference to FIG. 16. FIG. 16 is a block diagram showing a configuration of the living body detection sensor having a communication function. In the embodiment, data on measurement of a human body is sent to the outside by switching on the wireless communication depending on how close the human body is located to the living body detection sensor.

In the following, component portions which are the same as those of the third embodiment will be denoted by the same reference signs. Descriptions for such portions will be omitted, and descriptions will be provided for different portions only.

As shown in FIG. 16, a living body detection sensor 1100 has a communication function, and detects living body information (electrocardiographic information) on a human body 20. The living body detection sensor 1100 is provided with a signal generation unit 104, a detection unit 105, a control unit 106, a conductor 107, a conductor 108, a baseband unit 901, a high frequency unit 902, a switch 903, a switch 904, a high frequency unit 905, an antenna 906, an electrocardiograph 1101, a lowpass filter 1102, a lowpass filter 1103 and a user interface 1104.

In this respect, the signal generation unit 104, the detection unit 105, the control unit 106, the conductor 107 and the conductor 108 perform the same operations as those of the living body detection sensor 700 of the first embodiment. To put it specifically, the reception sensitivity becomes lower as the human body 20 comes closer to the living body detection sensor. The living body detection sensor detects the presence of the human body 20 once the received signal intensity detected by the detection unit 105 becomes equal to or less than a predetermined value.

The electrocardiograph 1101 receives electrocardiographic signals obtained from the human body 20 by use of the conductors 107, 108 which are in contact with the human body 20. The electrocardiograph 1101 includes a memory 1105 and a differential amplifier (not illustrated). The differential amplifier performs a differential amplification process. The electrocardiograph 1101 detects the electrocardiographic information, outputs the result of the detection to the control unit 106 in the form of a signal So2, and stores the electrocardiographic information in the memory 1105. The electrocardiograph 1101 outputs the detected electrocardiographic information to the baseband unit 901.

The lowpass filter 1102 is provided between the electrocardiograph 1101 and the conductor 107, and plays a role of preventing signals outputted from the high frequency unit 902 and the signal generation unit 104 from flowing into the electrocardiograph 1101. The lowpass filter 1103 is provided between the electrocardiograph 1101 and the conductor 108, and plays a role of preventing a first signal generated by the signal generation unit 104, which is sent from the conductor 108, from flowing into the electrocardiograph 1101.

The living body detection sensor 1100 performs wireless communication when data need to be transferred to an external apparatus. It should be noted that during the wireless communication, the electrocardiographic information may or may not continue to be detected. Even while no communication is performed, the control unit 106 sends the switch 903 a control signal Ssg1 in the enable state as long as the electrocardiographic information is being detected, for the purpose of recognizing that the conductors 107, 108 are in contact with the human body 20.

A signal So3 outputted from the control unit 106 is inputted into the user interface 1104. For this reason, while the living body detection sensor 1100 is working to detect the human body 20, or while the living body detection sensor 1100 is unable to detect the electrocardiographic information because the conductors 107, 108 are out of contact with the human body 20, a check can be made with the external apparatus by use of the user interface 1104.

As described above, the living body detection sensor of the embodiment includes the signal generation unit 104, the detection unit 105, the control unit 106, the conductor 107, the conductor 108, the baseband unit 901, the high frequency unit 902, the switch 903, the switch 904, the high frequency unit 905, the antenna 906, the electrocardiograph 1101, the lowpass filter 1102, the lowpass filter 1103 and the user interface 1104. The signal generation unit 104, the detection unit 105, the control unit 106, the conductor 107 and the conductor 108 jointly function as the living body detection sensor. While the human body 20 is in contact with the conductors 107, 108, the conductors 107, 108 receive the electrocardiographic signals obtained from the human body 20. The electrocardiograph 1101 receives the electrocardiographic signal outputted from the conductor 107 through the lowpass filter 1102, and the electrocardiographic signal outputted from the conductor 108 through the lowpass filter 1103. The electrocardiograph 1101 detects the electrocardiographic information, and outputs the result of the detection to the control unit 106. The user interface 1104 receives the signal outputted from the control unit 106.

Thereby, the living body detection sensor 1100 is capable of sending the data on the measurement by switching on the wireless communication depending on how close the human body is located to the living body detection sensor. In addition, regardless of whether or not the communication is performed, the living body detection sensor 1100 is capable of informing the outside of the fact as to whether or not the conductive bodies 107, 108 as the electrodes to detect the electrocardiography are in contact with the human body 20.

Figure 17:
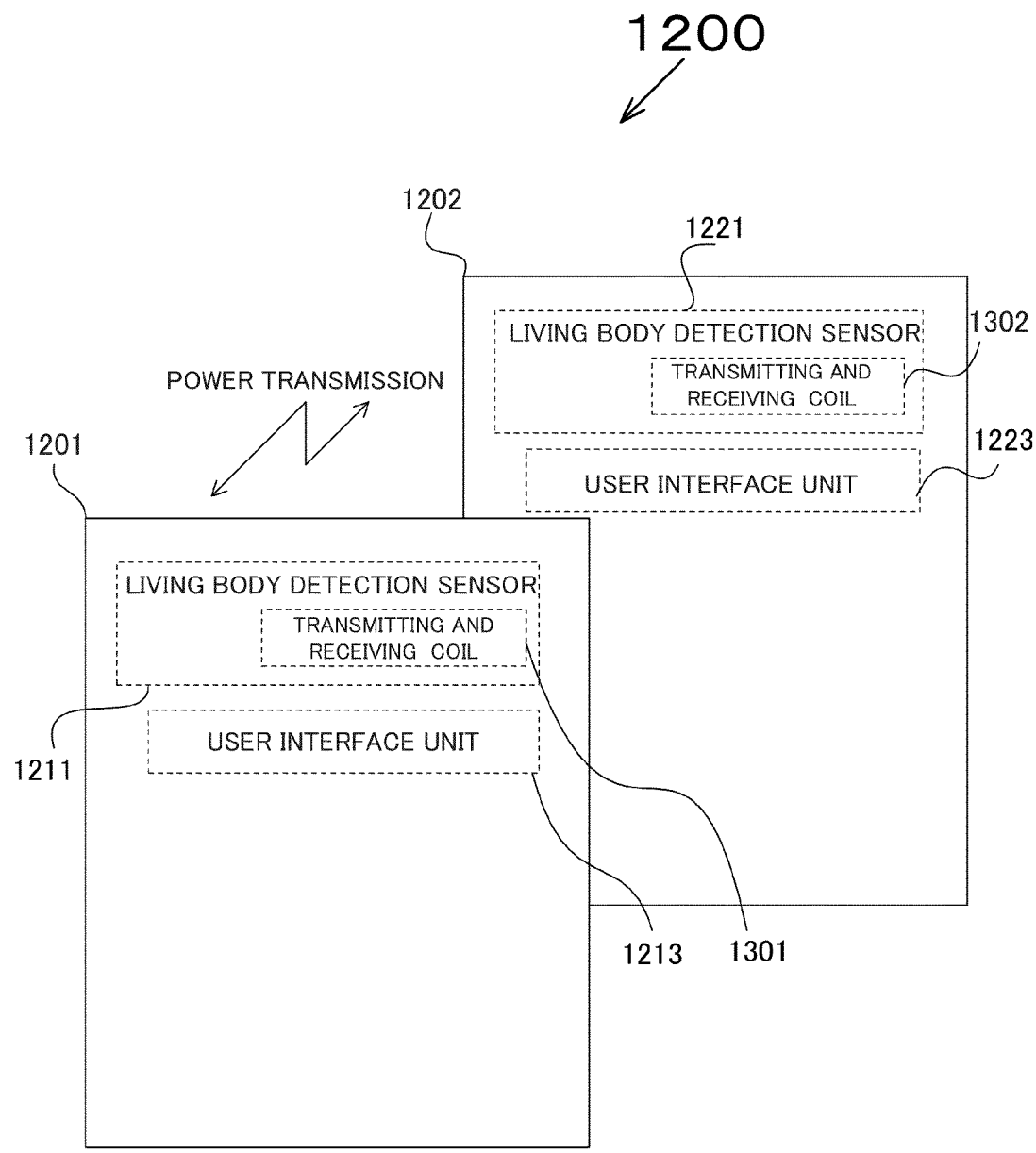
FIG. 17 is a schematic diagram showing a power transmission system according to a fifth embodiment.
Figure 18:
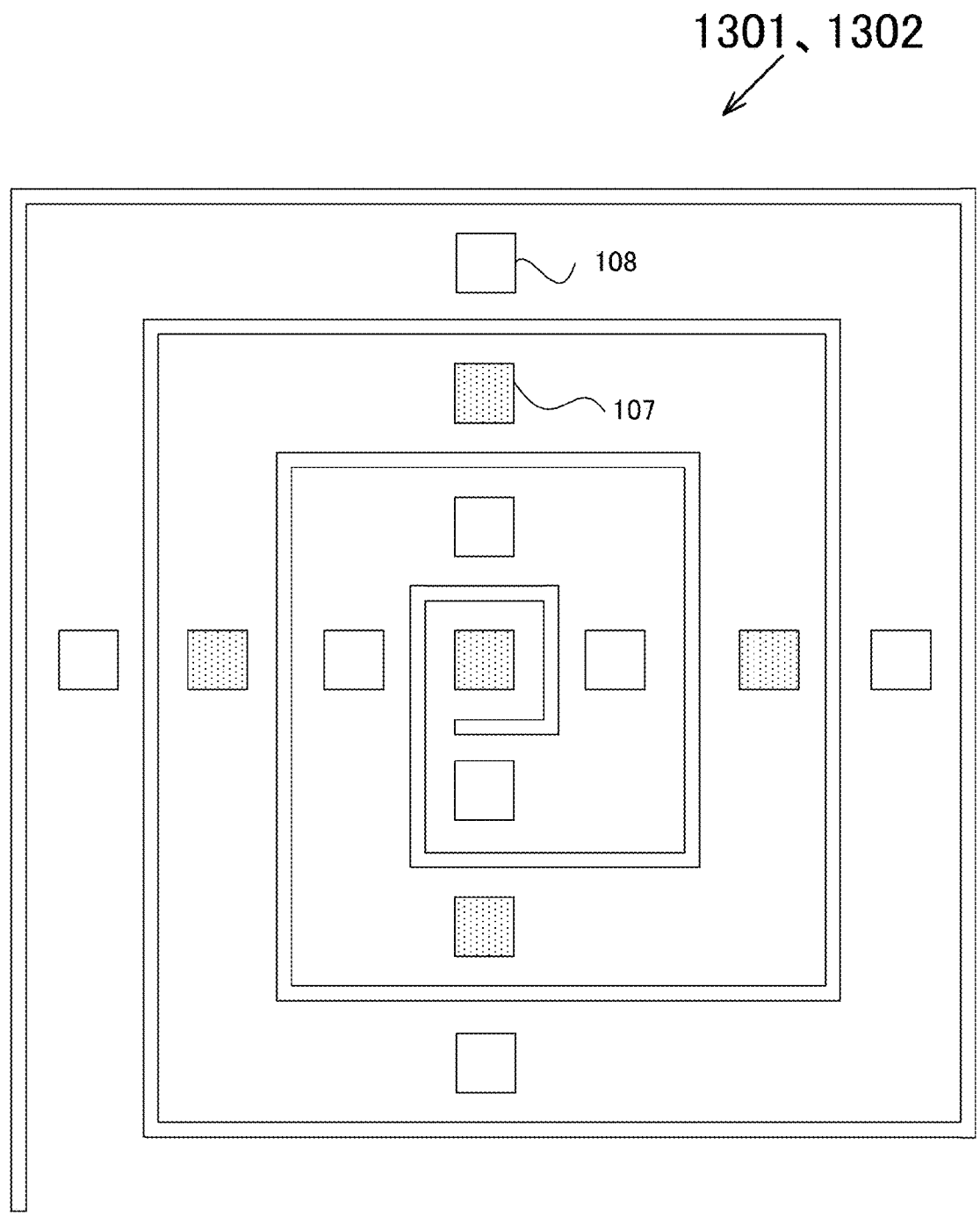
FIG. 18 is a plan view showing a coil of a power transmission apparatus according to the fifth embodiment.

A power transmission system of a fifth embodiment will be described with reference to FIGS. 17 and 18. FIG. 17 is a schematic diagram showing a configuration of the power transmission system. FIG. 18 is a plan view of a coil of a power transmission apparatus. In the embodiment, the power transmission apparatus is designed to be capable of detecting how close to a living body detection sensor a human body is located, by providing the transmission apparatus with the living body detection sensor, and providing conductive bodies of the living body detection sensor between each two adjacent loops of the coil of the power transmission apparatus.

As shown in FIG. 17, a power transmission system 1200 includes a power transmission apparatus 1201 and a power transmission apparatus 1202. In the power transmission system 1200, power is wirelessly transmitted between the power transmission apparatuses 1201, 1202.

Methods of wireless power transmission include electromagnetic induction, radio emission, magnetic resonance, and the like. The embodiment employs the magnetic resonance type wireless power transmission which offers higher power transmission efficiency even if the power transmission apparatuses 1201, 1202 are away from each other by several meters.

Generally speaking, the power transmission efficiency decreases when the living body such as the human body 20 is in contact with, or close to, a transmitting and receiving coil to function as a resonator for a transmitter. For this reason, in the embodiment, the power transmission apparatus 1201 includes a living body detection sensor 1211 and a user interface unit 1213, while the power transmission apparatus 1202 includes a living body detection sensor 1221 and a user interface unit 1223. The living body detection sensor 1211 includes a transmitting and receiving coil 1301, while the living body detection sensor 1221 includes a transmitting and receiving coil 1302.

Like the living body detection sensor 700 of the first embodiment, the living body sensors 1211, 1221 detect whether the living body such as the human body 20 is in contact with, or close to, the respective transmitting and receiving coils.

As shown in FIG. 18, in each of the transmitting and receiving coils 1301, 1302, conductors 107 and conductors 108 are alternately placed between each adjacent two of the multiple loops. The placement makes it possible to detect how close to the transmitting and receiving coil the living body as the human body is located with high sensitivity. The result of the detection by the living body detection sensor 1211 is outputted to the outside through the user interface unit 1213. The result of the detection by the living body detection sensor 1221 is outputted to the outside through the user interface unit 1223.

As described above, the power transmission system of the embodiment includes the power transmission apparatus 1201, 1202 between which the power is transmitted wirelessly. The power transmission apparatus 1201 includes the living body detection sensor 1211 and the user interface unit 1213. The living body detection sensor 1211 includes the transmitting and receiving coil 1301. The power transmission apparatus 1202 includes the living body detection sensor 1221 and the user interface unit 1223. The living body detection sensor 1221 includes the transmitting and receiving coil 1302.

This enables the power transmission system 1200 to detect whether or not the living body such as the human body 20 is located close to the power transmission apparatuses with high sensitivity, and to inform a user of the results of the detection quickly.

Figure 19:
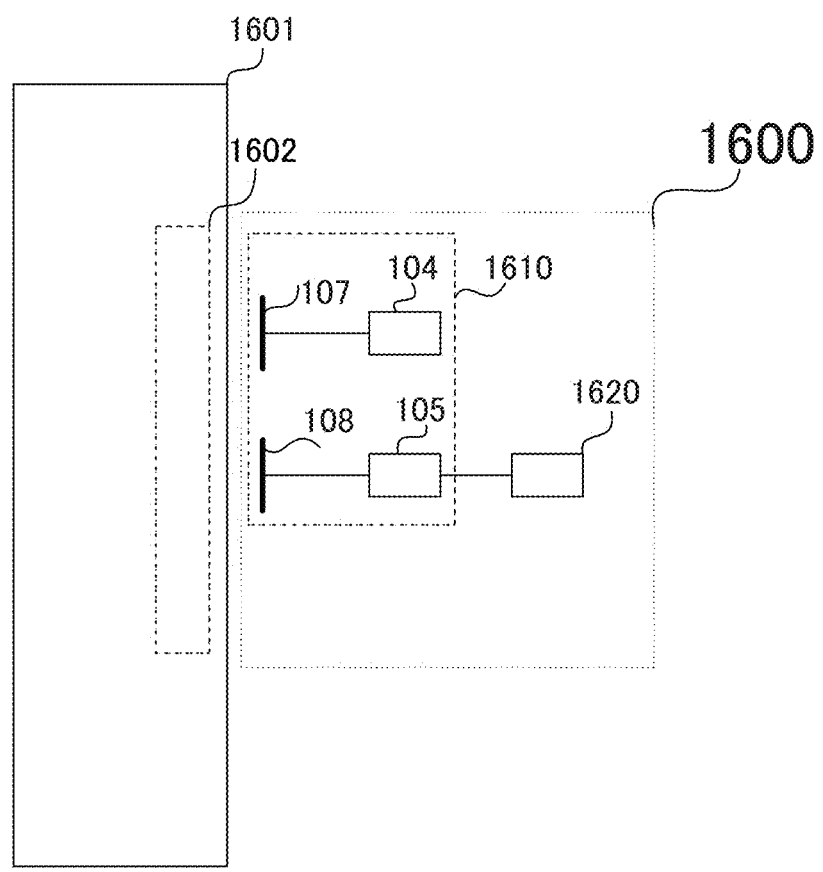
FIG. 19 is a schematic diagram showing a metal detection sensor according to a 6th embodiment.

A metal detection sensor of a 6th embodiment will be described with reference to FIG. 19. FIG. 19 is a schematic diagram of the metal detection sensor. In the embodiment, a piece of metal in an object is detected by use of the metal detection sensor.

In the following, component portions which are the same as those of the first embodiment will be denoted by the same reference signs. Descriptions for such portions will be omitted, and descriptions will be provided for the different portions only.

As shown in FIG. 19, a metal detection sensor 1600 includes a metal detection unit 1610 and a control unit 1620. The metal detection unit 1610 includes a signal generation unit 104, a detection unit 105, a conductor 107 and a conductor 108.

When the metal detection sensor 1600 searches the inside of an object 1601 for a piece of metal 1602, the metal detection sensor 1600 is brought close to or into contact with the object 1601. The metal detection sensor 1600 scans over the surface of the object 1601 by moving the metal detection unit 1610 by use of a position control unit (not illustrated), for example. The control unit 1620 controls the metal detection unit 1610, the position control unit, and the like. The metal detection unit 1610 detects the piece of metal 1602 in the object 1601, and sends the control unit 1620 the result of the detection.

The control unit 1620 associates the result of the detection by the metal detection unit 1610 with the position of the metal detection unit 1610, and stores the associated result and position in a memory (not illustrated). The position and shape of the piece of metal 1602 in the object 1601 can be detected through the scan over the surface of the object 1601.

Figure 20A:
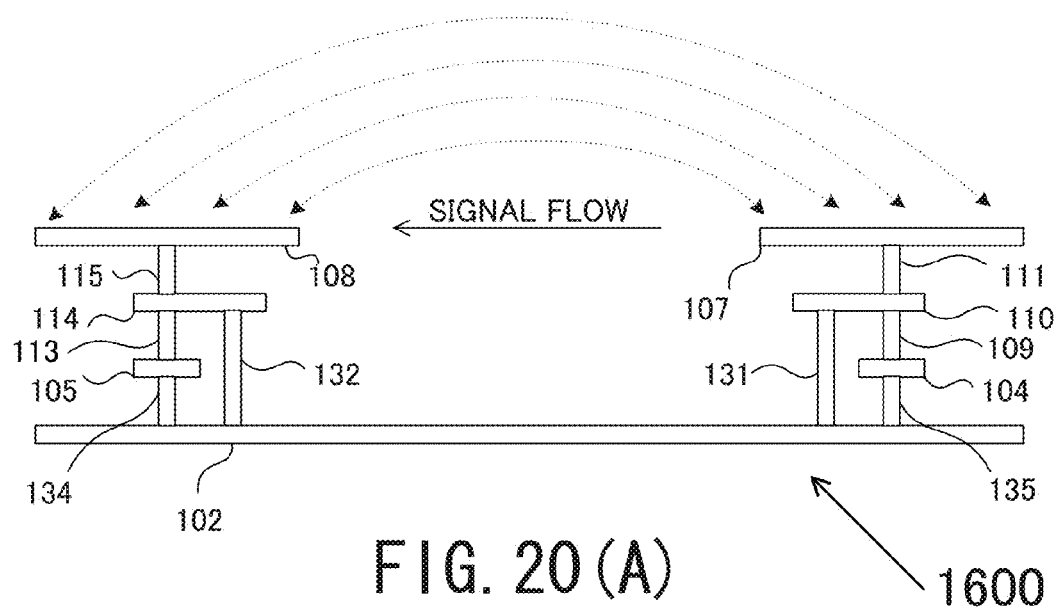
FIGS. 20(A) and 20(B) are diagrams for explaining an operation of the metal detection sensor according to the 6th embodiment.
Figure 20B:
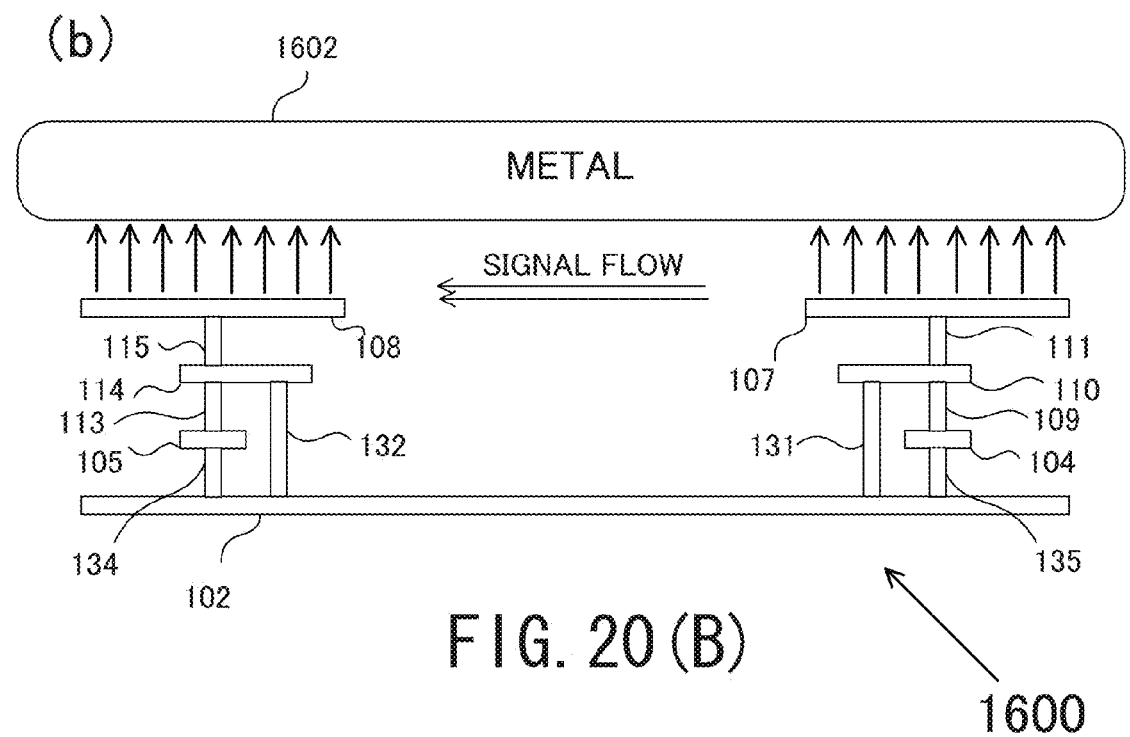

Next, descriptions will be provided for how the metal detection sensor 1600 detects a piece of metal with reference to FIGS. 20(A) and 20(B). FIG. 20(A) is a schematic diagram showing spatial coupling between the conductors 107, 108. FIG. 20(B) is a schematic diagram showing a case where the piece of metal 1602 is close to the metal detection sensor 1600.

As shown in FIG. 20(A), while the piece of metal 1602 is away from the metal detection sensor 1600, the conductors 107, 108 are spatially coupled to each other (in the same way as is shown in FIG. 4(A) for the first embodiment).

As shown in FIG. 20(B), when the piece of metal 1602 comes close to the metal detection sensor 1600, a first signal sent from the conductor 107 is transmitted along the surface of the piece of metal 1602. Accordingly, the signal intensity of the first signal received by the conductor 108 becomes higher than in the case shown in FIG. 20(A). The result is the opposite of the result in the case of the living body in the first embodiment.

Figure 21:
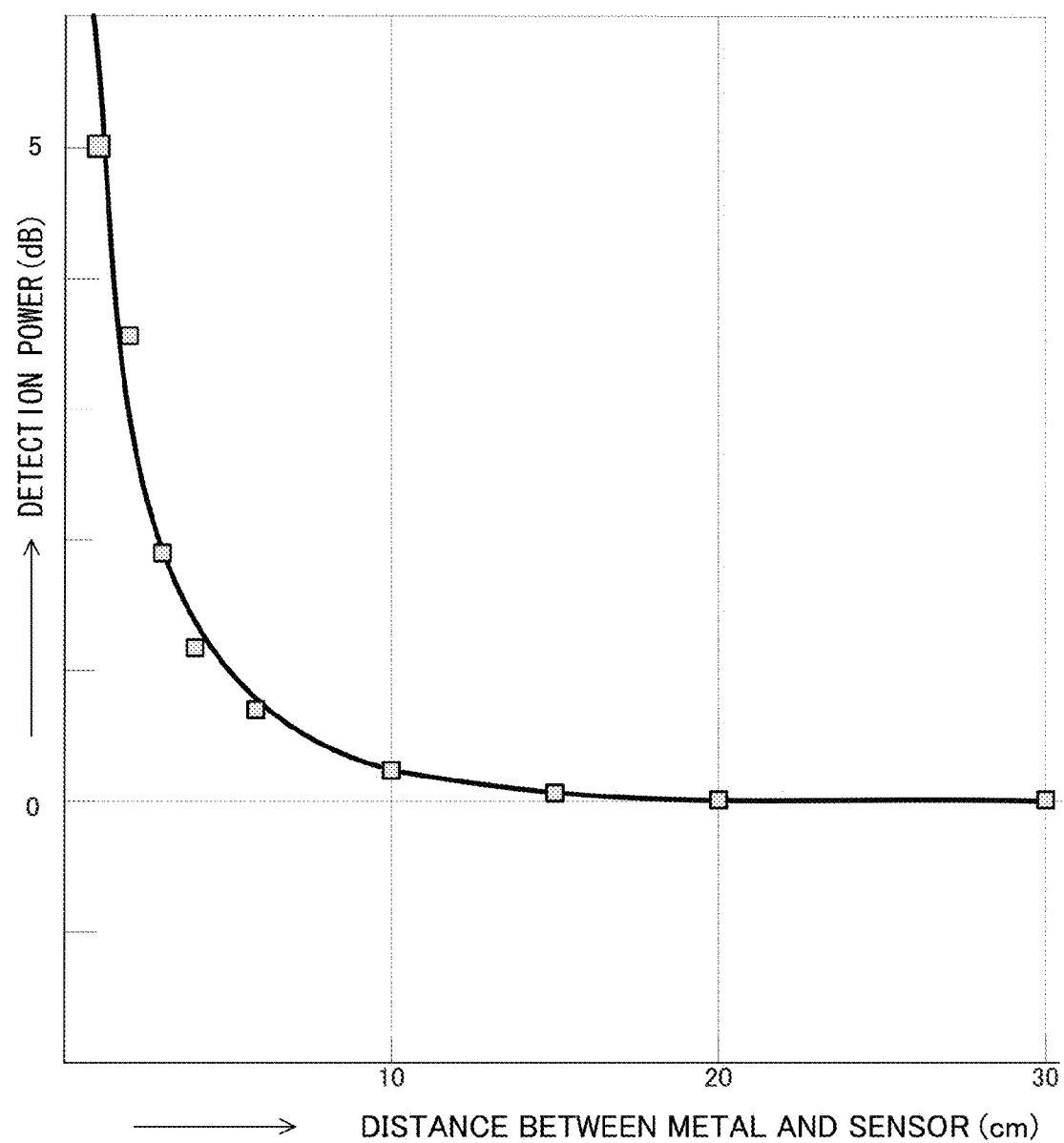
FIG. 21 is a diagram showing a relation of detection power with a distance between a piece of metal and the sensor in the 6th embodiment.

Next, detection characteristics of the metal detection sensor 1600 will be described with reference to FIG. 21. FIG. 21 is a diagram showing a relation between detection power and the distance between the piece of metal 1602 and the metal detection sensor 1600. In FIG. 21, the detection power is defined as standing at 0 (zero) dB while the piece of metal 1602 is away from the metal detection sensor 1600.

As shown in FIG. 21, when the distance between the piece of metal 1602 and metal detection sensor 1600 is equal to or greater than 20 cm, for example, the detection power stands at a constant 0 (zero) dB. When the distance between the piece of metal 1602 and the metal detection sensor 1600 becomes equal to 15 cm, the detection power starts to increase. When the distance between the piece of metal 1602 and the metal detection sensor 1600 becomes shorter, the detection power increases sharply. When the distance between the piece of metal 1602 and the metal detection sensor 1600 becomes equal to almost 0 cm, the detection power stands at +5 dB.

The result shows that the metal detection sensor 1600 is capable of detecting the piece of metal 1602 in spite of the relatively simple configuration, In FIG. 21, when the distance between the metal 1602 and the metal detection sensor 1600 becomes equal to 15 cm, the detection power starts to increase. For the purpose of making the metal detection sensor 1600 more highly sensitive, however, it is desirable that the capacitance coupling between the conductors 107, 108 be increased.

Figure 22:
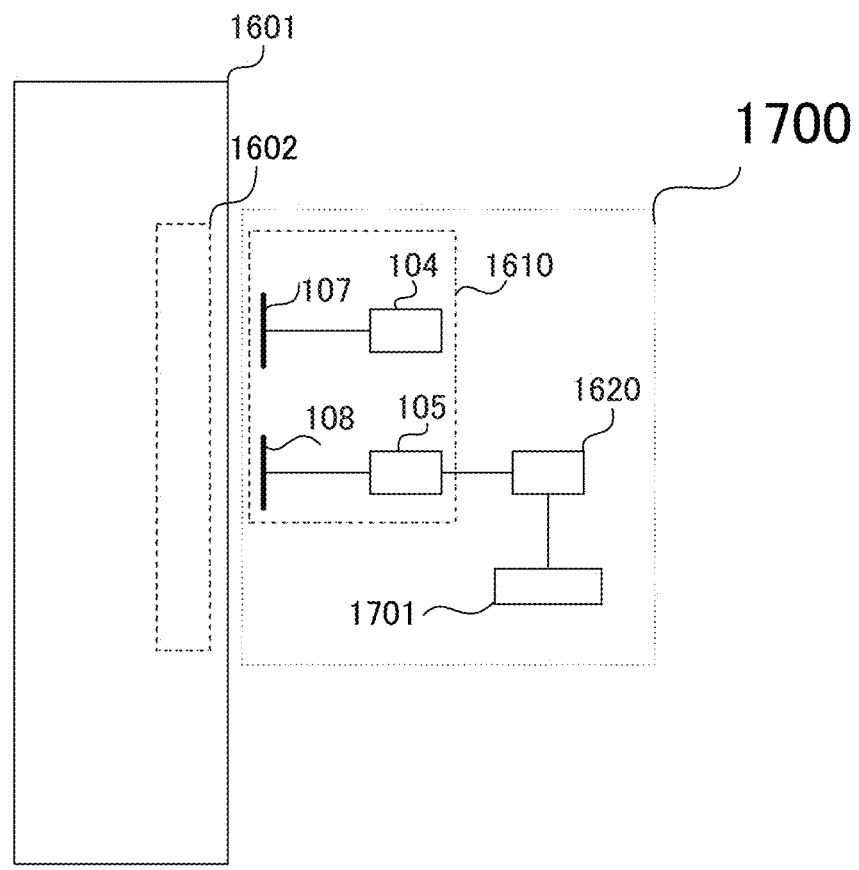
FIG. 22 is a schematic diagram showing a metal detection sensor according to a third modification.

The metal detection sensor 1600 of the embodiment may be provided with a camera. A camera 1701 may be connected to the control unit 1620, like in a metal detection sensor 1700 of a third modification shown in FIG. 22, for example. The camera 1701 sends the control unit 1620 data on a captured image. The control unit 1620 stores the result of the detection by the detection unit 1610 and the data on the image in the memory. The metal detection sensor 1700 creates data on a diagram onto which a contour map or an intensity distribution map is projected in accordance with the detection power in the data on the image. This enables the metal detection sensor 1700 to detect the position and shape of the piece of metal 1602 in the object 1601.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A living body detection sensor comprising:
an antenna;
a substrate including a reference potential electrode and a dielectric material;
a signal generator configured to generate a first signal, the signal generator being provided on the substrate;
a first conductor configured to receive the first signal and to output the first signal, the first conductor being separated from the substrate;
a second conductor configured to connect to the first conductor through a spatial coupling, to receive the first signal outputted from the first conductor, and to output the first signal, the second conductor being separated from the substrate; and
a detector configured to receive the first signal outputted from the second conductor and to detect a signal intensity of the first signal outputted from the second conductor, the detector being provided on the substrate, wherein
the living body detection sensor configured to detect a living body when the signal intensity detected by the detector changes and to perform communication by use of an electromagnetic field produced around the living body when a distance between the living body and the living body detection sensor is equal to or less than a predetermined distance, and by use of the antenna when the distance between the living body and the living body detection sensor is greater than the predetermined distance.

2. The sensor according to claim 1, further comprising a controller configured to control the detector, the controller being provided on the substrate and connected to the detector.

3. The sensor according to claim 2, further comprising:
a baseband unit;
a first switch;
a second switch;
a first high frequency unit; and
a second high frequency unit, wherein
the first high frequency unit is provided between the second switch and the antenna,
the second high frequency unit is provided between the second switch and the first conductor,
the first switch is provided between the signal generator and the first conductor, and is configured to connect or disconnect the signal generator and the first conductor on the basis of a first control signal from the controller, and
the second switch is configured to send and receive a signal to and from the baseband unit, and to connects the baseband unit and the first high frequency unit together, or the baseband unit and the second high frequency unit together, on the basis of a second control signal from the controller.

4. The sensor according to claim 3, further comprising:
an electrocardiograph;
a first lowpass filter;
a second lowpass filter; and
a user interface, wherein
the electrocardiograph is configured to:
receive electrocardiographic signals obtained from the living body by use of the first conductor and the second conductor which are configured to be in contact with the living body; and
output electrocardiographic information to the baseband unit,
the first lowpass filter is provided between the electrocardiograph and the first conductor,
the second lowpass filter is provided between the electrocardiograph and the second conductor,
the controller is configured to input the electrocardiographic information into the user interface; and
the living body sensor is configured to transmit the electrocardiographic information by switching communication to the antenna based on a measured distance between the living body and the living body detection sensor.

5. The sensor according to claim 1, wherein
the first conductor and the second conductor are each shaped like any one of a plate, a disk and an elliptic disk, and are placed opposite to each other.

6. The sensor according to claim 1, wherein
the second conductor is placed around the first conductor, and away from the first conductor by a predetermined distance.

7. The sensor according to claim 1, wherein
the substrate, the signal generator and the detector are housed in a housing.

8. The sensor according to claim 7, wherein
the first conductor and the second conductor are placed on an inner wall of the housing.

9. The sensor according to claim 7, wherein
the first conductor and the second conductor are placed on an outer wall of the housing.

10. The sensor according to claim 1, wherein
the first conductor and the second conductor are each composed of any one of a conductive sheet, a conductive ink and a transparent conductive material.

11. The sensor according to claim 1, wherein
each of the first conductor and the second conductor includes a plurality of conductors,
the living body detection sensor further comprises a transmitting and receiving coil,
the transmitting and receiving coil has a shape of a winding,
the first conductor and the second conductor are alternately placed between each adjacent two of winding loops,
the transmitting and receiving coil is configured to wirelessly transmit electric power, and
the living body detection sensor is configured to detect whether or not the living body is close to the transmitting and receiving coil.

12. The sensor according to claim 11, wherein
the living body detection sensor is provided in a power transmission apparatus, and
the power transmission apparatus is configured to wirelessly transmit the electric power using any one of magnetic resonance, electromagnetic induction and radio emission.

13. The sensor according to claim 1, wherein the detector is further configured to detect the change in the signal intensity of the first signal by detecting a disruption of the spatial coupling.

14. The sensor according to claim 1, wherein the spatial coupling is generated by an electric field produced between the first conductor and the second conductor.

15. The sensor according to claim 1, wherein the change in the signal intensity of the first signal is a decrease in the signal intensity.

* * * * *